(12) United States Patent
Jaeger et al.

(10) Patent No.: US 8,852,882 B2
(45) Date of Patent: Oct. 7, 2014

(54) BIOSENSORS AND THEIR USE

(75) Inventors: Karl Erich Jaeger, Mülheim (DE);
Thomas Drepper, Stolberg (DE);
Stephan Endres, Düsseldorf (DE);
Janko Potzkei, Düsseldorf (DE); Achim Heck, Mönchengladbach (DE); Franco Circolone, Krefeld (DE)

(73) Assignee: Evocatal GmbH, Dusseldorf (DE)

( * ) Notice: Subject to any disclaimer, the term of this patent is extended or adjusted under 35 U.S.C. 154(b) by 0 days.

(21) Appl. No.: 13/817,743

(22) PCT Filed: Aug. 16, 2011

(86) PCT No.: PCT/EP2011/064059
§ 371 (c)(1),
(2), (4) Date: Jun. 11, 2013

(87) PCT Pub. No.: WO2012/022728
PCT Pub. Date: Feb. 23, 2012

(65) Prior Publication Data
US 2013/0280749 A1    Oct. 24, 2013

(30) Foreign Application Priority Data
Aug. 16, 2010   (DE) .......................... 10 2010 037 001

(51) Int. Cl.
| | | |
|---|---|---|
| *C12Q 1/02* | (2006.01) | |
| *G01N 21/76* | (2006.01) | |
| *G01N 31/16* | (2006.01) | |
| *G01N 31/22* | (2006.01) | |
| *C12Q 1/00* | (2006.01) | |
| *G01N 33/542* | (2006.01) | |
| *C07K 14/00* | (2006.01) | |
| *G01N 33/58* | (2006.01) | |

(52) U.S. Cl.
CPC ........ *C12Q 1/02* (2013.01); *C12Q 1/008* (2013.01); *G01N 33/542* (2013.01); *C07K 14/00* (2013.01); *G01N 33/582* (2013.01); *Y10S 435/968* (2013.01)
USPC ............. 435/29; 435/968; 436/172; 436/163

(58) Field of Classification Search
CPC ............. C12Q 1/02; C12Q 1/00; C07K 14/00
See application file for complete search history.

(56) References Cited

U.S. PATENT DOCUMENTS

2007/0059690 A1*  3/2007  Islam et al. .................... 435/6
2009/0098596 A1*  4/2009  Jares-Erijman et al. ........ 435/29
2009/0227043 A1*  9/2009  Huang ........................... 436/501

FOREIGN PATENT DOCUMENTS

DE   102005048828 A1   4/2007

OTHER PUBLICATIONS van der Krogt et al, A Comparison of Donor-Acceptor Pairs for Genetically Encoded FRET Sensors: Application to the Epac cAMP Sensor as an Example, PLoS ONE 3(4): e1916. doi:10.137, p. 1-9.*
Zeiss, Education in Microscopy and Digital Imaging, retrieved online on Dec. 31, 2013 from URL:<http://zeiss-campus.magnet.fsu.edu/articles/probes/jellyfishfps.html>.*
Yi I. Wu et al., "A genetically encoded photoactivatable Rac controls the motility of living cells", Nature, Sep. 3, 2009, 461(7260), pp. 104-108.
International Search Report, PCT/EP2011/064059, dated Nov. 23, 2011, 5 pages.
Baird et al., "Circular permutation and receptor insertion within green fluorescent proteins", Proc Natl Acad Sci USA, Sep. 28, 1999;96(20), pp. 11241-11246.
Mank et al., "A FRET-based calcium biosensor with fast signal kinetics and high fluorescence change", Biophys J. Mar. 1, 2006;90(5), pp. 1790-1796.
Pickup et al., "Fluorescence-based glucose sensors", Biosensors and Bioelectronics, 20 (2005), pp. 2555-2565.
Yano et al., "A Novel Fluorescent Sensor Protein for Visualization of Redox States in the Cytoplasm and in Peroxisomes", Mol Cell Biol. Aug. 2010; 30(15), pp. 3758-3766.

* cited by examiner

*Primary Examiner* — Marcela M Cordero Garcia
*Assistant Examiner* — Sergio Coffa
(74) *Attorney, Agent, or Firm* — Senniger Powers LLP

(57) ABSTRACT

A FRET donor-acceptor pair for use as a biosensor, comprising at least two fluorescence proteins, wherein at least one fluorescence protein is stable with respect to a parameter to be detected by the biosensor and at least one fluorescence protein is unstable with respect to the parameter to be detected by the biosensor.

2 Claims, 13 Drawing Sheets

SEQUENCE LISTING

<160> NUMBER OF SEQ ID NOS: 16

<210> SEQ ID NO 1
<211> LENGTH: 720
<212> TYPE: DNA
<213> ORGANISM: Aequorea victoria

<400> SEQUENCE: 1

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 2
<211> LENGTH: 239
<212> TYPE: PRT
<213> ORGANISM: Aequorea victoria

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95
```

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Tyr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 3
<211> LENGTH: 447
<212> TYPE: DNA
<213> ORGANISM: Pseudomonas putida

<400> SEQUENCE: 3
atgatcaacg caaaactcct gcaactgatg gtcgaacatt ccaacgatgg catcgttgtc      60
gccgagcagg aaggcaatga gagcatcctt atctacgtca acccggcctt cgagcgcctg     120
accggctact gcgccgacga tattctctat caggacgccc gttttcttca gggcgaggat     180
cacgaccagc cgggcatcgc aattatccgc gaggcgatcc gcgaaggccg ccctgctgc      240 caggtgctgc gcaactaccg caaagacggc agcctgttct ggaacgagtt gtccatcaca     300
ccggtgcaca acgaggcgga ccagctgacc tactacatcg catccagcg cgatgtcaca      360 gcgcaagtat tcgccgagga aagggttcgc gagctggagg ctgaagtggc ggaactgcgc     420
cggcagcagg gccaggccaa gcactga                                         447

<210> SEQ ID NO 4
<211> LENGTH: 148
<212> TYPE: PRT
<213> ORGANISM: Pseudomonas putida

<400> SEQUENCE: 4

Met Ile Asn Ala Lys Leu Leu Gln Leu Met Val Glu His Ser Asn Asp
1               5                   10                  15

Gly Ile Val Val Ala Glu Gln Glu Gly Asn Glu Ser Ile Leu Ile Tyr
                20                  25                  30

Val Asn Pro Ala Phe Glu Arg Leu Thr Gly Tyr Cys Ala Asp Asp Ile
            35                  40                  45

Leu Tyr Gln Asp Ala Arg Phe Leu Gln Gly Glu Asp His Asp Gln Pro
    50                  55                  60

Gly Ile Ala Ile Ile Arg Glu Ala Ile Arg Glu Gly Arg Pro Cys Cys
65                  70                  75                  80

Gln Val Leu Arg Asn Tyr Arg Lys Asp Gly Ser Leu Phe Trp Asn Glu
                85                  90                  95

Leu Ser Ile Thr Pro Val His Asn Glu Ala Asp Gln Leu Thr Tyr Tyr
                100                 105                 110

Ile Gly Ile Gln Arg Asp Val Thr Ala Gln Val Phe Ala Glu Glu Arg
            115                 120                 125

Val Arg Glu Leu Glu Ala Glu Val Ala Glu Leu Arg Arg Gln Gln Gly
        130                 135                 140

Gln Ala Lys His
145

<210> SEQ ID NO 5
<211> LENGTH: 406
<212> TYPE: DNA
<213> ORGANISM: Artificial
<220> FEATURE:
<223> OTHER INFORMATION: Sequence of FbFP optimized for expression
      in E.coli

<400> SEQUENCE: 5
atggcgtcgt tccagtcgtt cggcatcccg ggccagctgg aagtcatcaa gaaggcgctg     60
gatcacgtgc gcgtcggcgt ggtcatcacc gatcccgcgc tggaagataa cccgatcgtc    120
tacgtgaacc agggcttcgt gcagatgacc ggctacgaga ccgaggaaat cctgggcaag    180
aacgcgcgct tcctccaggg gaagcacacc gatccggcgg aagtggacaa catccgcacc    240
gcgctgcaaa ataaagaacc ggtcaccgtg cagatccaga actacaagaa ggacggcacg    300
atgttctgga cgaactgaa catcgatccg atggaaatcg aggataagac gtatttcgtc     360
ggcatccaga cgacatcac caagcagaag gaatatgaaa agctgc                    406

<210> SEQ ID NO 6
<211> LENGTH: 134
<212> TYPE: PRT
<213> ORGANISM: Artificial
<220> FEATURE:
<223> OTHER INFORMATION: Protein relating to SEQ ID No 5

<400> SEQUENCE: 6

Ala Ser Phe Gln Ser Phe Gly Ile Pro Gly Gln Leu Glu Val Ile Lys
1               5                   10                  15

Lys Ala Leu Asp His Val Arg Val Gly Val Val Ile Thr Asp Pro Ala
            20                  25                  30

Leu Glu Asp Asn Pro Ile Val Tyr Val Asn Gln Gly Phe Val Gln Met
        35                  40                  45

Thr Gly Tyr Glu Thr Glu Glu Ile Leu Gly Lys Asn Ala Arg Phe Leu
    50                  55                  60

Gln Gly Lys His Thr Asp Pro Ala Glu Val Asp Asn Ile Arg Thr Ala
65                  70                  75                  80

Leu Gln Asn Lys Glu Pro Val Thr Val Gln Ile Gln Asn Tyr Lys Lys
                85                  90                  95

Asp Gly Thr Met Phe Trp Asn Glu Leu Asn Ile Asp Pro Met Glu Ile
            100                 105                 110

Glu Asp Lys Thr Tyr Phe Val Gly Ile Gln Asn Asp Ile Thr Lys Gln
        115                 120                 125

Lys Glu Tyr Glu Lys Leu
    130

<210> SEQ ID NO 7
<211> LENGTH: 783
<212> TYPE: DNA
<213> ORGANISM: Bacillus subtilis

<400> SEQUENCE: 7

```
atggctagtt ttcaatcatt tgggatacca ggacagctgg aagtcatcaa aaaagcactt    60
gatcacgtgc gagtcggtgt ggtaattaca gatcccgcac ttgaagataa tcctattgtc   120
tacgtaaatc aaggctttgt tcaaatgacc ggctacgaga ccgaggaaat tttaggaaag   180
aacgcacgct tcttacaggg gaaacacaca gatcctgcag aagtggacaa catcagaacc   240
gctttacaaa ataaagaacc ggtcaccgtt cagatccaaa actacaaaaa agacggaacg   300
atgttctgga tgaattaaa tattgatcca atggaaatag aggataaaac gtattttgtc   360
ggaattcaga atgatatcac caagcaaaaa gaatatgaaa agcttctcga ggattccctc   420
acggaaatta ctgcactttc aactcctatt gtcccgattc gcaatggcat ttcggctctt   480
ccgctagtcg gaaacctgac agaggagcga tttaattcca tcgtttgcac attgacgaat   540
atcttatcaa catccaaaga tgattatttg atcattgatt tatccggatt ggcccaagtg   600
aacgaacaaa cggccgacca aatttttcaag ctgagccatt tgctgaaatt gaccggaact   660
gagttaatca ttactggcat taagcctgaa ttggctatga aaatgaataa actggatgcc   720 aattttttcgt cgctgaaaac atattcaaat gtaaaggatg ccgttaaagt gcttccgatt   780
atg                                                                 783
```

<210> SEQ ID NO 8
<211> LENGTH: 260
<212> TYPE: PRT
<213> ORGANISM: Bacillus subtilis

<400> SEQUENCE: 8

```
Ala Ser Phe Gln Ser Phe Gly Ile Pro Gly Gln Leu Glu Val Ile Lys
  1               5                  10                  15

Lys Ala Leu Asp His Val Arg Val Gly Val Val Ile Thr Asp Pro Ala
             20                  25                  30

Leu Glu Asp Asn Pro Ile Val Tyr Val Asn Gln Gly Phe Val Gln Met
         35                  40                  45

Thr Gly Tyr Glu Thr Glu Glu Ile Leu Gly Lys Asn Ala Arg Phe Leu
     50                  55                  60

Gln Gly Lys His Thr Asp Pro Ala Glu Val Asp Asn Ile Arg Thr Ala
 65                  70                  75                  80

Leu Gln Asn Lys Glu Pro Val Thr Val Gln Ile Gln Asn Tyr Lys Lys
                 85                  90                  95

Asp Gly Thr Met Phe Trp Asn Glu Leu Asn Ile Asp Pro Met Glu Ile
            100                 105                 110

Glu Asp Lys Thr Tyr Phe Val Gly Ile Gln Asn Asp Ile Thr Lys Gln
        115                 120                 125

Lys Glu Tyr Glu Lys Leu Leu Glu Asp Ser Leu Thr Glu Ile Thr Ala
    130                 135                 140

Leu Ser Thr Pro Ile Val Pro Ile Arg Asn Gly Ile Ser Ala Leu Pro
145                 150                 155                 160

Leu Val Gly Asn Leu Thr Glu Glu Arg Phe Asn Ser Ile Val Cys Thr
                165                 170                 175

Leu Thr Asn Ile Leu Ser Thr Ser Lys Asp Asp Tyr Leu Ile Ile Asp
            180                 185                 190

Leu Ser Gly Leu Ala Gln Val Asn Glu Gln Thr Ala Asp Gln Ile Phe
        195                 200                 205

Lys Leu Ser His Leu Leu Lys Leu Thr Gly Thr Glu Leu Ile Ile Thr
    210                 215                 220
```

```
Gly Ile Lys Pro Glu Leu Ala Met Lys Met Asn Lys Leu Asp Ala Asn
225                 230                 235                 240

Phe Ser Ser Leu Lys Thr Tyr Ser Asn Val Lys Asp Ala Val Lys Val
            245                 250                 255

Leu Pro Ile Met
            260
```

```
<210> SEQ ID NO 9
<211> LENGTH: 1230
<212> TYPE: DNA
<213> ORGANISM: Artificial
<220> FEATURE:
<223> OTHER INFORMATION: Sequence for the fusion protein of YFP and FbFP

<400> SEQUENCE: 9
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccttcggcta cggcctgcag tgcttcgccc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctgggccac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagct accagtccgc cctgagcaaa gaccccaacg agaagcgcga tcacatggtc       660
ctgctggagt tcgtgaccgc cgccgggatc actctcggca tggacgagct gtacaaggag       720
ctcgcgggcc tggtgccgcg cggcagcggc gccgtcgaca tgatcaacgc aaaactcctg       780
caactgatgg tcgaacattc aacgatggc atcgttgtcg ccgagcagga aggcaatgag        840
agcatcctta tctacgtcaa cccggccttc gagcgcctga ccggctactg cgccgacgat       900
attctctatc aggacgcacg ttttcttcag ggcgaggatc acgaccagcc gggcatcgca       960
attatccgcg aggcgatccg cgaaggccgc ccctgctgcc aggtgctgcg caactaccgc      1020
aaagacggca gcctgttctg gaacgagttg tccatcacac cggtgcacaa cgaggcggac      1080
cagctgacct actacatcgg catccagcgc gatgtcacag cgcaagtatt cgccgaggaa      1140
agggttcgcg agctggaggc tgaagtggcg gaactgcgcc ggcagcaggg ccaggccaag      1200
cacctcgagc accaccacca ccaccactga                                       1230
```

```
<210> SEQ ID NO 10
<211> LENGTH: 409
<212> TYPE: PRT
<213> ORGANISM: Artificial
<220> FEATURE:
<223> OTHER INFORMATION: Amino acid sequence relating to SEQ ID No 9

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                      70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Glu
225                 230                 235                 240

Leu Ala Gly Leu Val Pro Arg Gly Ser Gly Ala Val Asp Met Ile Asn
                245                 250                 255

Ala Lys Leu Leu Gln Leu Met Val Glu His Ser Asn Asp Gly Ile Val
            260                 265                 270

Val Ala Glu Gln Glu Gly Asn Glu Ser Ile Leu Ile Tyr Val Asn Pro
            275                 280                 285

Ala Phe Glu Arg Leu Thr Gly Tyr Cys Ala Asp Asp Ile Leu Tyr Gln
            290                 295                 300

Asp Ala Arg Phe Leu Gln Gly Glu Asp His Asp Gln Pro Gly Ile Ala
305                 310                 315                 320

Ile Ile Arg Glu Ala Ile Arg Glu Gly Arg Pro Cys Cys Gln Val Leu
                325                 330                 335

Arg Asn Tyr Arg Lys Asp Gly Ser Leu Phe Trp Asn Glu Leu Ser Ile
            340                 345                 350

Thr Pro Val His Asn Glu Ala Asp Gln Leu Thr Tyr Tyr Ile Gly Ile
            355                 360                 365

Gln Arg Asp Val Thr Ala Gln Val Phe Ala Glu Arg Val Arg Glu
            370                 375                 380

Leu Glu Ala Glu Val Ala Glu Leu Arg Arg Gln Gln Gly Gln Ala Lys
385                 390                 395                 400

His Leu Glu His His His His His
            405

<210> SEQ ID NO 11
<211> LENGTH: 26
<212> TYPE: DNA
<213> ORGANISM: Artificial
<220> FEATURE:
<223> OTHER INFORMATION: Upper Primer PpFbFP FRET-Fusion (SalUp)

<400> SEQUENCE: 11
gtcgacatga tcaacgcaaa actcct                                      26

<210> SEQ ID NO 12
<211> LENGTH: 20
<212> TYPE: DNA
<213> ORGANISM: Artificial
<220> FEATURE:
<223> OTHER INFORMATION: Down Primer PpFbFP FRET-Fusion (XhoIDown)

<400> SEQUENCE: 12
ctcgaggtgc ttggcctggc                                             20

<210> SEQ ID NO 13
<211> LENGTH: 19
<212> TYPE: DNA
<213> ORGANISM: Artificial
<220> FEATURE:
<223> OTHER INFORMATION: Upper Primer YFP FRET-Fusion (NdeIUp)

<400> SEQUENCE: 13
catatggtga gcaagggcg                                              19

<210> SEQ ID NO 14
<211> LENGTH: 25
<212> TYPE: DNA
<213> ORGANISM: Artificial
<220> FEATURE:
<223> OTHER INFORMATION: Down Primer YFP FRET-Fusion (SacIDown)

<400> SEQUENCE: 14
gagctccttg tacagctcgt ccatg                                       25

<210> SEQ ID NO 15
<211> LENGTH: 50
<212> TYPE: DNA
<213> ORGANISM: Artificial
<220> FEATURE:
<223> OTHER INFORMATION: Upper Primer Linker FRET-Fusion

<400> SEQUENCE: 15
ggtacccata tgggatccga gctcgcgggc ctggtgccgc gcggcagcgg            50

<210> SEQ ID NO 16
<211> LENGTH: 50
<212> TYPE: DNA
<213> ORGANISM: Artificial
<220> FEATURE:
<223> OTHER INFORMATION: Down Primer Linker FRET-Fusion

<400> SEQUENCE: 16
ccgcggctcg agaagcttgt cgacggcgcc gctgccgcgc ggcaccaggc            50

BIOSENSORS AND THEIR USE

REFERENCE TO RELATED APPLICATIONS

This application is a U.S. national stage application of International Patent Application No. PCT/EP2011/064059, filed Aug. 16, 2011, and claims the priority benefit of German Application No. 102010037001.0, filed Aug. 16, 2010, the entire disclosures of which are incorporated herein by reference.

FIELD OF THE INVENTION

The present invention relates to FRET donor-acceptor pairs for use as biosensors.

BACKGROUND OF THE INVENTION

In general, biosensors are defined as integrated measuring systems in which biological recognition structures interact with suitable analytes. In such systems, a physico-chemical signal is produced by the biosensor which can be transformed, via a transducer in the steric vicinity, into a measurable value. Such biosensors are in widespread use in clinical diagnostics, environmental analysis, food analysis, process control and fundamental research. In contrast to physical or chemical biosensors, which usually contain a synthetic component, biological biosensors are formed from biomacromolecules such as nucleic acids (DNA/RNA) or proteins; proteins are very good biosensors because they can highly specifically recognize the widest variety of molecules in cells and can bind with high affinity.

Using such biosensors, metal ions, various sugars such as glucose, nucleic acids or certain chemicals can be detected by means of different interactions with the biosensor. Furthermore, biosensors can contribute to analysing biological processes such as, for example, post-translational modifications, protein-protein interactions, enzyme activities as well as the detection of physical cell parameters such as the pH or the concentration of specific metabolites such as chloride ions in living organisms. Depending on the signal to be detected and the transducer, detection can be made in a variety of manners. Thus, biosensors can be detected optically, electrically, electrochemically, thermally or magnetically.

A further highly specific and sensitive possibility of efficiently detecting a signal by means of a biosensor is the transfer of the signal by fluorescence. To this end, recombinant fluorescence reporter proteins have been developed which either (1) interact directly with the substrate or signal to be determined via a specific sensor domain, whereupon the fluorescence domains fluoresce only in their presence or absence, or (2) the fluorescence properties of a fluorescence domain are directly changed by a change in the cell parameters or cell metabolites, such as a variation in pH. Thus, zinc ions can be detected by means of a modified eYFP (insertion of a zinc finger domain), or calcium ions can be detected by inserting calmodulin into the permutated eYFP.

In order to be able to resolve and detect even small variations, for example cell-specific signals, metabolites or proteins, more and more biosensors have been developed which are based on a Förster resonance energy transfer (FRET) system.

In order to be able to observe the fluorescence-resonance phenomenon, two chromophores with coordinated optical properties are required: a so-called donor and an acceptor. The purpose of the donor is the selective absorption of light emitted by a light source and its subsequent re-radiation, which as a rule is shifted to longer wavelengths. The absorption maximum of the acceptor lies in this emission spectrum, so that it can take up the emitted energy. In general, then, the emission of the acceptor indicates an energy transfer from donor to acceptor, which is described as FRET. The efficiency of the FRET is dependent on a number of factors. Thus, the emission band of the donor must have a sufficient overlap with the absorption band of the acceptor. Furthermore, the separation "r" and the orientation of the chromophores with respect to each other play an important role. In order to obtain a sufficiently intensive signal, "r" should be between 10 and 100 Å. Furthermore, the spatial orientation of the dyes is extremely important as regards the intensity of the energy transfer. This is non-radiative and directional and thus can only take place if the transition dipole moments of the donor and acceptor are orientated as parallel as possible to each other. The development of FRET biosensors means that it is now possible to detect or identify complex cell processes, cell parameters or protein interactions in fundamental research and in biotechnology with far more precision, since the dependency of the fluorescence signal on two fluorescence reporters means that the sensitivity of the signal recognition is greatly increased.

Since the investigation of reaction pathways in living systems and also the identification of the molecules involved therein is very difficult, there is a significant need for analytical methods to be developed which can deliver results rapidly and efficiently. Processes such as protein folding, protein interactions with each other or with DNA or RNA, and reactions of enzymes with their respective substrates are in need of a method for the separation-dependent examination of such processes; thus, FRET systems are also of particular interest as biosensors. With the aid of this "molecular tool", it is possible to follow separation changes on the nm-scale in real time, and so it is particularly suitable for the in vitro and in vivo analysis of biochemical events.

However, the search for FRET biosensors is very labour-intensive, since the emission bands of the donor must have a sufficiently large overlap with the absorption band of the acceptor. As a rule, therefore, comprehensive experimentation has to be carried out for each and every possible FRET pair.

Until now, green fluorescent protein (GFP) and related fluorescence proteins have been used for single biosensors or as FRET pairs or biosensors.

GFP and its colour variants (for example YFP, yellow fluorescent protein) are in widespread use in many areas of fundamental research and in biotechnology: fluorescent proteins are used for the investigation of gene-regulatory mechanisms or to monitor biotechnological processes. Fluorescence reporters may even be used to investigate cellular differentiation processes and to localize the respective target proteins in the cell. They may also be used to monitor folding processes in heterologous proteins in bacterial expression strains.

GFP or related proteins are used in FRET reactions, for example to assay many and varied ions in eukaryotes and also in prokaryotes and in specific cell types such as nerve cells. With the first FRET-based calcium sensor, it was possible to determine the concentration of $Ca^{2+}$ ions in cells (Baird et al, 1999); in 2006, Marco Mank's group optimized the speed of the fluorescence intensity change and demonstrated this with the $Ca^{2+}$ biosensor in nerve cells (Mank et al., 2006).

The fact that the FRET signal and thus also the fluorescence intensity reduces with increasing separation of the FRET partners was used to produce a glucose biosensor (Pickup et al. 2004).

Furthermore, it is now possible to use FRET reactions for the local investigation of various redox processes and physical variables in different cell compartments. Thus, in 2010, Yano et al detected and identified physiological and pathogenic redox states, and thus also pH changes, in peroxisomes using the redoxfluor biosensor.

Despite these various possibilities, there are still a lot of questions which have not yet been answered or have not yet been answered with sufficient accuracy using currently known FRET pairs.

Thus, it would be highly advantageous if further FRET pairs could be provided which reacted, or reacted more sensitively than presently known FRET pairs, to changes in cell parameters or metabolites such as, for example, $O_2$ concentration, variations in pH, temperature changes and changes in specific ion concentrations.

SUMMARY OF THE INVENTION

Thus, the aim of the present invention is to provide a FRET donor-acceptor pair for use as a biosensor which is capable of improving the detection of biorelevant parameters.

This aim is achieved by means of a FRET donor-acceptor pair in accordance with claim 1 and the use thereof in accordance with claim 4, as well as a method in accordance with claim 9.

DETAILED DESCRIPTION OF PREFERRED EMBODIMENTS

Figure 1:
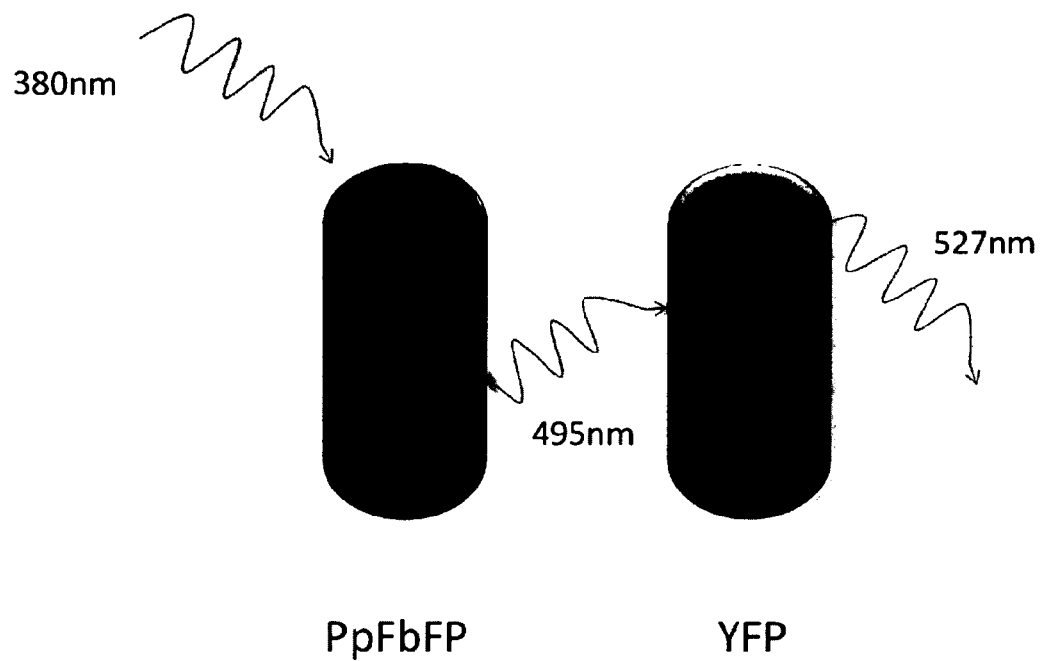
FIG. 1 shows the diagram of a FRET system.

Thus, a FRET donor-acceptor pair for use as a biosensor is provided, comprising at least two fluorescence proteins, wherein at least one fluorescence protein is stable with respect to a parameter to be detected by the biosensor and at least one fluorescence protein is unstable with respect to the parameter to be detected by the biosensor.

The term "fluorescence protein" should be understood to mean a protein which can fluoresce. Thus, the property of fluorescence can be generated by binding a chromophore or fluorophore to specific regions of a protein, for example to a LOV domain, or the property of fluorescence is encoded in the peptide sequence of the protein, such as that in GFP. After excitation of the fluorescence protein with light of a specific wavelength, fluorescence occurs. Most of the time, excitation results in short-lived, spontaneous emission of light when an electronically excited system changes to a lower energy state, whereby the emitted light is usually lower in energy than that which was absorbed.

The term "FRET" as used below should be understood to mean the physical process of energy transfer by means of Förster resonance energy transfer (abbreviated to FRET). In the context of Förster resonance energy transfer, the energy of an excited donor is transferred to an acceptor.

The term "donor" as used below should be understood to mean the fluorescence protein which is excited by irradiation with light and which transfers energy to an acceptor.

The term "acceptor" as used below should be understood to mean the fluorescence protein which takes up the energy of the donor resulting from irradiation with light.

The term "FRET donor-acceptor pair" as used below should be understood to mean a pair of fluorescence proteins wherein the emission band of the donor has a sufficiently large overlap with the absorption band of the acceptor to allow a transfer of energy with associated emission of fluorescence. It is possible for the FRET donor-acceptor pair to comprise other proteins in addition to the donor and the acceptor.

The term "biosensor" as used below should be understood to mean a biological sensor which comprises biomacromolecules such as nucleic acids (DNA/RNA) or proteins.

The term "stable" as used below should be understood to mean that a fluorescence protein is essentially not influenced by the parameter to be detected within the observed range of parameters. Conversely, the term "unstable" or "labile" as used below should be understood to mean that a fluorescence protein is measurably influenced by the parameter to be detected within the observed range of parameters.

Surprisingly, the genetically coded FRET donor-acceptor pair in accordance with the invention can be used for a more precise investigation of changes in cell parameters than previously known FRET pairs.

This is the case because at least one fluorescence protein of the FRET pair is stable with respect to a parameter to be detected by the biosensor, while at least one other fluorescence protein is labile with respect to the parameter to be detected by the biosensor. This means that the at least one property, for example the fluorescence property of the labile protein changes when the parameter to be detected changes. The change can be measured by observing the fluorescence ratio of the at least two fluorescence proteins. If, for example, the pH is examined in a specific range, then preferably, one fluorescence protein is selected which has properties which do not change in the range to be investigated, and one fluorescence protein is selected which has at least one property which can be influenced by the pH in the range to be investigated.

Preferred properties which can be influenced by the parameters to be measured are selected from the group comprising:
fluorescence;
chromophore binding;
chromophore maturation;
chromophore properties (for example absorption and fluorescence properties);
structural change;
change in covalent and non-covalent binding.

Preferably, the FRET donor-acceptor pair for use as a biosensor comprises exactly two fluorescence proteins.

The FRET donor-acceptor pair in accordance with the invention may, for example, be used as a biosensor in diagnostics, for example for screening enzyme functions. This can be used both for assigning unknown enzymes to the correct enzyme class, for the identification of possible substrates and thus the elucidation of the specificity of the enzyme, and also to the discovery of possible enzyme inhibitors, which are interesting as potential active ingredients. FRET systems satisfy these requirements very well, both because of the simple, direct detection of a specific signal and also by their broad field of application; thus, they are being used to an ever-increasing extent.

In one embodiment of the invention, at least two fluorescence proteins of the FRET donor-acceptor pair carry different chromophores.

The term "chromophore" as used below should be understood to mean specific groups in the molecule which affect the absorption behaviour of the compound in a characteristic manner.

Preferably, the chromophore is a fluorophore, i.e. an element in a molecule which is responsible for the fluorescence property of the molecule. Thus, the fluorophore is the part of a fluorescence protein which absorbs incident light of a specific wavelength and then re-emits it. Thus, the term "fluorophore" means both a molecule which binds the fluorescence protein and also specific peptide sequence(s) within the fluorescence protein.

An example of a molecule which is bound by a fluorescence protein as a fluorophore is flavin mononucleotide, while the tripeptide sequence $Ser_{65}$-$Tyr_{66}$-$Gly_{67}$ of GFP is an example of a peptide sequence which is present within a fluorescence protein as a fluorophore. It should be noted that the functional structure of the tripeptide sequence $Ser_{65}$-$Tyr_{66}$-$Gly_{67}$ is a 4-(p-hydroxy-benzylidene)-imidazolid-5-one, which is formed by cyclization with subsequent oxidation of the tripeptide.

Preferably, the chromophores are selected from the group comprising:
flavin mononucleotide (FMN);
riboflavin;
flavin adenine dinucleotide (FAD);
4-(p-hydroxybenzylidene)-imidazolidin-5-one and its derivatives.

This embodiment has the advantage that because the chromophores are different, the at least two fluorescence proteins react differently to many of the parameters to be measured and thus the change in the respective parameters can be detected.

This is precisely not the case when GFP and its colour variants are used, since all of those proteins react to changes in cell parameters in an identical or at least similar manner because they are related.

In a further embodiment of the invention, at least one fluorescence protein is oxygen-independent and at least one fluorescence protein is oxygen-dependent.

The term "oxygen-independent" as used below should be understood to mean that a fluorescence protein requires no oxygen for chromophore synthesis, while the term "oxygen-dependent" should be understood to mean that a fluorescence protein requires oxygen for chromophore synthesis.

All fluorescence proteins of the GFP family without exception form the chromophore in a multi-step autobiocatalysis process. Since in this process, molecular oxygen is required, maturation of the chromophore and thus the formation of the fluorescence signal is directly dependent on this environmental factor.

Thus, the uses of GFP and its derivatives as a fluorescence reporter protein is limited to aerobic systems and the fluorescence signal of these proteins cannot be used in anaerobic organisms or under hypoxic conditions.

Thus, the FRET donor-acceptor pair of the invention is particularly advantageous since for the first time, the possibility arises of highly sensitively determining different oxygen concentrations in vivo and in vitro using a genetically coded FRET donor-acceptor pair.

What is more, the FRET donor-acceptor pair of the invention is particularly advantageous, since it can also be used in anaerobic systems.

Preferably, at least one of the at least two fluorescence proteins of the FRET donor-acceptor pair of the invention is a LOV protein.

The term "fluorescence protein comprising a LOV domain" as used below should be understood to mean a protein which comprises a light, oxygen or voltage (LOV) domain, in which at least one cysteine is replaced by another amino acid and also in which, in addition to the exchange of the at least one cysteine, at least one point mutation is present. LOV domain proteins bind the cofactors FMN, FAD or riboflavin prepared by the host organism in a different manner to GFP-like fluorescence proteins. These molecules are synthesized oxygen-independently in prokaryotes and also in eukaryotes.

Examples of proteins comprising a LOV domain are the blue light receptor YtvA from *B. subtilis* and the sensory box protein SB2 from *Pseudomonas putida*.

The blue light receptor YtvA is a 261 amino acid protein which was classified as a putative protein kinase during the complete genome sequencing of *B. subtilis*. It plays a role as a positive regulator in the $\sigma^B$-mediated stress response of *B. subtilis*. YtvA could be identified, by means of sequence homology comparisons, with the primary structure of plant blue light receptors, phototropins. YtvA consists of an N-terminal LOV domain and a C-terminal STAS (sulphate transporter antisigma) domain. The LOV domain exhibits a special folding motif formed by a 5-stranded anti-parallel β-sheet with sides flanked by α-helices. The LOV domain contains the consensus sequence NCRFLQG known from plant phototropins, wherein the photoactive cysteine contained in it covalently binds the FMN cofactor as a chromophore during the LOV-specific photocycle. In this regard, excitation with light at a wavelength of 450 nm causes the YtvA to change over from the ground state into a photoproduct which absorbs at 383 nm and has an emission maximum of 498 nm. Within a short time period (approx. 1.6 μs), this photoproduct decays to a photoadduct in which the FMN is covalently bound. In this form, the LOV domain loses its property of fluorescence until the ground state is regained.

By using sequence homology comparisons of the LOV domain of YtvA from *B. subtilis* with the genome sequence of the gram-negative rod bacterium *P. putida* KT2440, a gene was identified therein which encodes a putative LOV protein. It is the 151 amino acid SB2 (sensory box 2), which contains only one LOV domain. The SB2 protein has the characteristic consensus sequence of LOV domains. Because the photoactive region has been located, the photocycle of sensory box 2 proteins has been investigated.

Preferably, the at least one cysteine in the LOV domain is replaced by alanine.

Further, particularly preferably, at least one of the at least two fluorescence proteins of the FRET donor-acceptor pair of the invention is a FbFP protein.

Recently, a completely novel fluorescence protein family comprising LOV domains or recombinant variations of bacterial blue light receptors of the LOV family has been developed. In contrast to fluorescence proteins like GFP, the novel fluorescence markers are very small (16-19 kDa). In order to increase the FMN-dependent fluorescence of the blue light receptors and thus to allow them to be used as fluorescence markers, the bacterial proteins were changed using up-to-date procedures known as directed evolution. By means of such mutations, auto-fluorescence of the proteins was drastically increased, whereupon FMN-binding fluorescence proteins (FbFPs) were produced, in particular the FbFP from *P. putida* KT2440 (SEQ ID No. 4) and the FbFPs from *B. subtilis* (SEQ ID No. 8 or SEQ ID No. 6). The novel marker proteins can be expressed in various prokaryotic and eukaryotic host cells and the characteristic fluorescence of FbFP has been demonstrated in vivo. The photochemical characterization of the novel marker proteins showed that the FbFPs emit a blue-green fluorescence (495 nm) after excitation with blue light (450 nm).

Thus, "FMN-based fluorescence proteins" (FbFP)s constitute fluorescence reporter proteins which fluorescence independently of the oxygen partial pressure. In contrast to representatives of the GFP family, FbFP does not need oxygen to fluoresce.

Further, a preferred FRET donor-acceptor pair for use as a biosensor comprises a fusion protein formed from a FbFP protein and a GFP-related protein.

The description "a GFP-related protein" should be understood to mean a protein which has a structure similar to GFP such as, for example, yellow fluorescence protein (YFP), cyan fluorescence protein (CFP) and enhanced green fluorescence protein (eGFP). In addition, the term "YFP-related protein" should be understood to mean a protein which has a structure similar to YFP.

Surprisingly, it has been shown that a fusion protein formed from a FbFP protein and a GFP-related protein can be used as a FRET pair. This could not be predicted since the emission bands of the donor have to have a sufficiently large overlap with the absorption bands of the acceptor.

The fusion protein formed from a FbFP protein and a GFP-related protein has many advantages. Thus, this FRET donor-acceptor pair can be used both in vivo and in vitro in a multitude of manners for the quantitative determination of the most varied parameters, such as pH, oxygen and halide ion concentration, as well as for the detection of riboflavin, FAD, FMN or for the observation of temperature changes.

In contrast to established GFP-based biosensors, for the first time, with this preferred FRET donor-acceptor pair, for the first time, it is possible to determine different oxygen concentrations in vivo as well as in vitro with a high degree of sensitivity. Direct determination of $O_2$ concentrations would be of immense assistance in cancer therapy and also in many biotechnological areas.

Figure 9:
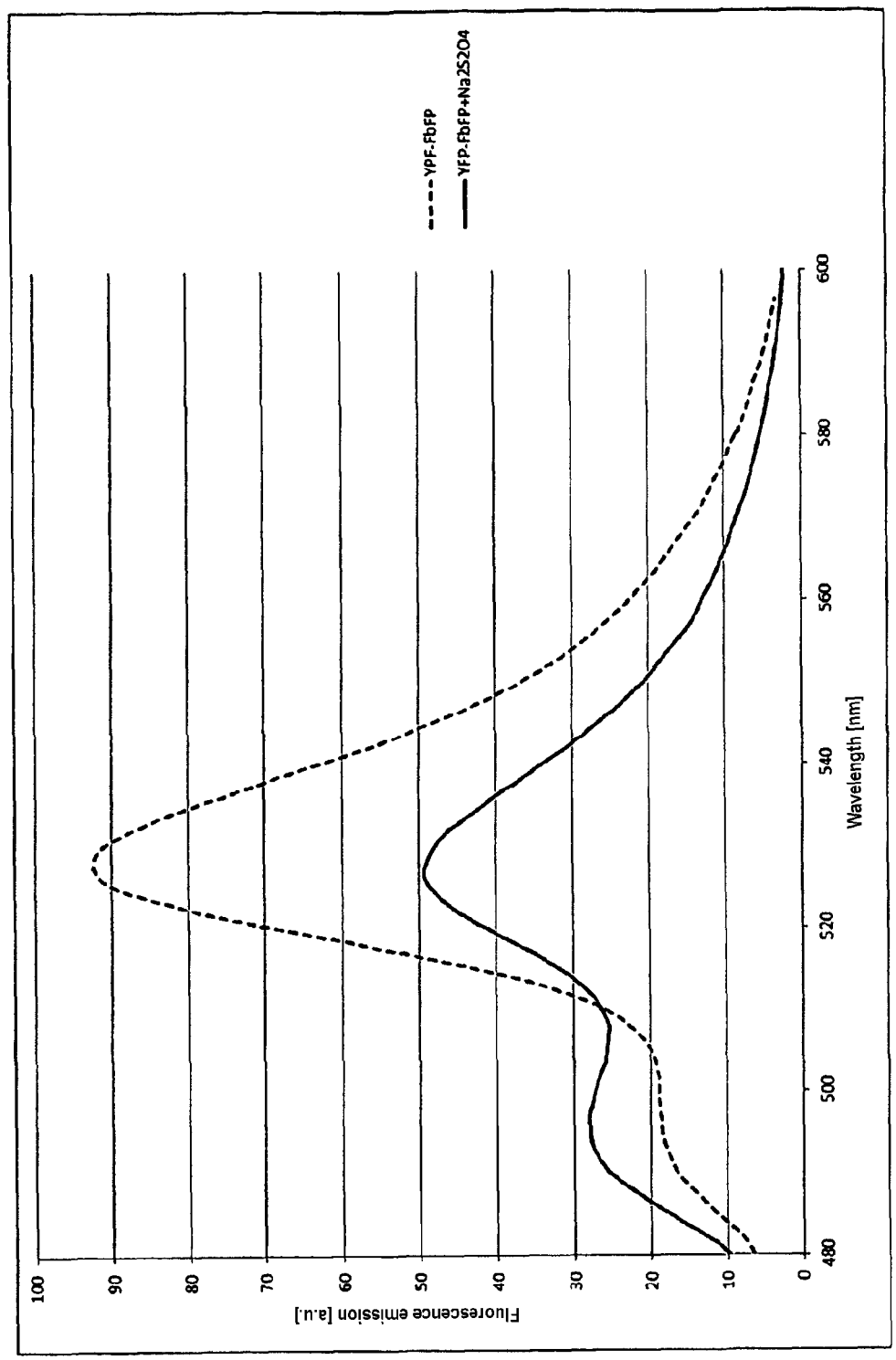
FIG. 9 shows the fluorescence photometric measurement of the Na2S2O4 reduction of the YFP chromophore.

As can be seen in FIG. 9, with the aid of the fusion protein formed from a FbFP protein and a GFP-related protein, it is possible to detect the current oxygen concentration with the help of the ratio of the two fluorescence maxima at $\lambda=527$ nm/495 nm, so that the oxygen concentration in the cell and/or the system can be obtained directly. The fusion protein formed from a FbFP protein and a GFP-related protein is thus particularly applicable to the investigation or optimization of metabolic processes or expression studies in aerobic and anaerobic cells or systems in biotechnology, in cancer research and also in basic research in the investigation of oxygen limitations in cells.

Further, the use of the fusion protein produced from a FbFP protein and a GFP-related protein may be envisaged for the investigation of bacterial biofilms and hypoxic tissues. Bacteria such as the human pathogenic bacterium *Pseudomonas aeroginosa* are usually organized into small groups bonded to biotic and abiotic surfaces, which quite often can trigger infections (biofilm formation). However, in biofilms, oxygen limitation plays an important role for cells which lie in the deeper layers. With a fusion protein formed from a FbFP protein and a GFP-related protein, we have available an outstanding tool for detecting microaerobic areas in biofilms and simultaneously to elucidate mechanisms and inter-relations in the biofilms under anaerobic conditions by means of the oxygen-independent FMN-based fluorescence protein (FbFP) contained in the FRET system.

Surprisingly, it has turned out that the preferred FRET donor-acceptor pair can also be used for determining the pH, since clearly the fluorescence intensity of a FbFP protein is not dependent on the various pHs, but the intensity of fluorescence of a GFP-related protein is pH-dependent.

In addition, a fusion protein formed from a FbFP protein and a GFP-related protein surprisingly has a much higher pH sensitivity than comparable FRET systems.

This higher pH sensitivity, which is accompanied by a greater possibility of resolution as a function of pH, is advantageous with respect to other pH biosensors, since the fluorescence ratio of FbFP and YFP is in the range from 0.5 to 5. In contrast, the corresponding fluorescence ratio in other biosensors in this field of application is only in the range of 1 to 2 (Yano et al. 2010). pH variations can thus be detected far more precisely with the fusion protein formed from a FbFP protein and a GFP-related protein.

As an example, the fusion protein formed from a FbFP protein and a GFP-related protein may be used in lifetime pH imaging in cells such as, for example, in lysosomes or peroxisomes, where the pH in various cell compartments can be determined in vivo during different growth phases, even in acid ranges.

Furthermore, the fusion protein formed from a FbFP protein and a GFP-related protein may be very effectively employed in the determination or localization of different ion concentrations such as chloride or iodide since, in contrast to established biosensors, it has a higher FRET ratio range and thus can react far more sensitively to changes in the ion concentration to be detected because of a higher dynamic range. Above all, the GFP-related protein is influenced by a varying halide concentration, which results in a differing intensity of fluorescence emission; this is presumably the result of the ions influencing protein folding. Thus, the fusion protein formed from a FbFP protein and a GFP-related protein is suitable for use in the neurobiological field, for example.

A further possible field of application of the fusion protein formed from a FbFP protein and a GFP-related protein is the use as a temperature biosensor in cancer therapy. This is within the realm of possibility, since fluorescence measurements have shown that the reactions of FbFPs in temperature ranges from 30° C. to 65° C. as opposed to the GFP-related proteins are far more sensitive to temperature.

This difference in the temperature stability of the individual proteins can be exploited in the FRET system. Different fluorescence emission ratios at suitable temperatures, for example from 30° C. to 60° C., can be measured, so that the various fluorescence emission ratios can give direct access to the temperature.

Moreover, because of the dependency of the FbFP fluorescence signal on the FMN, FAD or riboflavin cofactors, the preferred FRET donor-acceptor pair can be used for the detection of riboflavin in cells and tissues. A molecular riboflavin sensor is of great importance in many areas of (molecular) medicine. As an example, it might contribute to a better understanding of riboflavin depletion events and resulting symptoms such as corneal degeneration, night blindness or other symptoms.

Preferably, the GFP-related protein is YFP.

Particularly preferably, the YFP is the acceptor and the FbFP protein is the donor of the FRET donor-acceptor pair.

This preferred FRET donor-acceptor pair is based on a translational fusion between the YFP and a FbFP fluorescence protein in which the FbFP fluorescence domain is C-terminally fused to the YFP target protein. The two proteins are thus bonded via a linker (see FIG. 2).

Furthermore, the invention provides for the use of a complex formed from a protein with a LOV domain and a fluorescence protein for resonance energy transfer, wherein either the donor or the acceptor of the resonance energy transfer system can fluoresce in an anaerobic medium.

The term "complex" as used below should be understood to mean that the two proteins are close to each other in space. This can be brought about in a variety of manners, for example by covalent and non-covalent binding, such as biotin-streptavidin binding.

The term "anaerobic medium" as used below should be understood to mean conditions under which relatively little or no oxygen is available for reactions, such as metabolic processes or catalysis.

The term "can fluoresce" as used below should be understood to mean that a fluorescence protein can be excited by light of a specific wavelength and/or that the energy absorbed upon excitation can be re-released.

The use of a complex of this type is advantageous, since it enables resonance energy transfer to be carried out even in an anaerobic medium or under low-oxygen conditions. As mentioned above, this is not possible with prior art complexes, for example complexes formed from different proteins of the GFP protein family.

In one embodiment of this use, the donor is a protein with a LOV domain.

This is advantageous, since proteins with a LOV domain fluoresce or can be excited in an anaerobic medium. Thus, complexes formed from a protein with a LOV domain used as a donor and a fluorescence protein as an acceptor can be used for oxygen measurement. In this, a reduction of the oxygen content results in a reduced energy transfer of the oxygen-independent protein with a LOV domain to the oxygen-dependent acceptor. This results in a reduction in the fluorescence signal of the acceptor if the oxygen content falls. Thus, for the first time it is possible to determine oxygen via the relative ratio of the signals of the donor and the acceptor.

In a further embodiment of this use, the acceptor is a YFP-related protein, i.e. a protein which comprises an amino acid sequence:
 a) in accordance with SEQ ID No. 2 or a fragment, a variant, a homologue or a derivative of said sequence;
 b) which has a sequence identity of at least 70%, preferably 95% with one of the amino acid sequences from (a).

A YFP-related protein as the acceptor, in particular in combination with a protein with a LOV domain as the donor, has the advantage that the differing structures of the various chromophores ensures that the two proteins react differently to many of the parameters to be measured, and thus the change in the parameter can be detected by resonance energy transfer.

In a further embodiment of this application, the protein with a LOV domain:
 a) is encoded by a nucleic acid with SEQ ID No. 3, 5 or 7 or a fragment, a variant, a homologue or a derivative of one of these sequences;
 b) is encoded by a nucleic acid which can hybridize with one of the nucleic acids from a) under stringent conditions;
 c) is encoded by a nucleic acid which has at least 70%, preferably 95% identity with one of the nucleic acids from a) or b);
 d) is encoded by a nucleic acid which can hybridize under stringent conditions with the complementary nucleic acid of one of the nucleic acids from a)-c);
 e) is encoded by a nucleic acid which, compared with the nucleic acids from a)-d), has at least one silent mutation of a single nucleotide (as allowed by the degeneration of the genetic code);
 f) is encoded by a nucleic acid the code for which has been optimized for a specific expression system compared with the nucleic acids from a)-e);
 g) comprises an amino acid sequence in accordance with one of SEQ ID No. 4, 6 or 8 or a fragment, a variant, a homologue or a derivative of one of these sequences; and/or
 h) comprises an amino acid sequence which has a sequence identity of at least 70%, preferably 95% with one of the amino acid sequences from g).

The term "nucleic acid" as used below should be understood to mean a single or double-stranded macromolecule which is formed from nucleotides. The most common nucleic acids are deoxyribonucleic acid (DNA) or complementary DNA (cDNA) and ribobucleic acid (RNA). DNA contains the nucleobases adenine, cytosine, guanine and thymine, the latter being specific to DNA. RNA contains the same nucleobases or nucleotides, except that thymine is replaced by uracil. Examples of synthetic nucleic acids are peptide nucleic acid (PNA), morpholino and locked nucleic acid (LNA), as well as glycol nucleic acid (GNA) and threose nucleic acid (TNA). The construction of the backbone of each of these nucleic acids differs from nucleic acids of natural origin.

The term "complementary" as used below should be understood to mean the nucleic acids which are complementary to the used/discussed nucleic acids. This is an important concept in molecular biology, since it concerns an important property of double-stranded nucleic acids such as DNA, RNA or DNA:RNA duplexes. One strand is complementary to the other in that the base pairs of both strands are bonded non-covalently via two or three hydrogen bonds. In principle—there are exceptions for thymine/uracil and the wobble complex of tRNA—there is only one complementary base for each base of a nucleic acid. Thus, it is possible to reconstruct the complementary strand of a given individual strand. This is essential to DNA replication, for example. As an example, the complementary strand for the DNA sequence:

```
a. 5' A G T C A T G 3'
is b. 3' T C A G T A C 5'
```

In the case of DNA, the term "complementary" can also denote cDNA. cDNA is synthesized using the reverse transcriptase enzyme from RNA, for example mRNA.

The term "hybridize" or "hybridization" as used below should be understood to mean the procedure whereby a nucleic acid becomes bonded to a more or less completely complementary nucleic acid with the formation of hydrogen bonds between the respective complementary nucleobases.

The term "hybridize under stringent conditions" as used below should be understood to mean that the conditions for the hybridization reaction are set such that only completely complementary bases can form hydrogen bonds. The stringency may be influenced by the temperature, for example.

The term "silent mutation" as used below should be understood to mean the phenomenon whereby a mutation in a section of a nucleotide acid does not result in any consequences. In such a case, the information content of the gene is not changed, because an amino acid chain is encoded by different groups of three successive nucleobases—known as triplets or codons.

The term "fragment" as used below should be understood to denote a portion of a nucleic acid or an amino acid sequence wherein some parts are missing a given nucleic acid or an amino acid sequence, but wherein at least a part of its activity, for example as regards fluorescence properties, enzyme activity, or binding to other molecules, is retained.

The term "variant" as used below should be understood to mean a nucleic acid or an amino acid sequence which has a structure and biological activity which is essentially the same as the structure and biological activity of a specific nucleic acid or an amino acid sequence.

The term "derivative" as used below should be understood to mean a related nucleic acid or amino acid sequence which has similar characteristics with respect to a target molecule as a given nucleic acid or amino acid sequence.

The term "homologue" as used below should be understood to mean a nucleic acid or an amino acid sequence the sequence of which has at least one nucleotide or an amino acid which has been added, deleted, substituted or modified in another manner compared with the sequence of a given nucleic acid or amino acid sequence. However, the homologue must have essentially the same properties as the given nucleic acid or amino acid sequence.

The term "optimized for a specific expression system" as used below should be understood to mean that a nucleic acid is matched to the codon usage of the organism in which it is expressed. The codon usage, or codon bias, describes the phenomenon that variants of the universal genetic code are often used in different ways by different species.

The term "sequence identity of at least X %" as used below should be understood to mean a sequence identity determined by sequence alignment using a BLAST algorithm available on the homepage of the NCBI.

In a further embodiment of the use, the donor-acceptor pair is genetically coded and/or is a fusion protein and/or is expressed together as a transcriptional unit.

In contrast to non-genetically coded donor-acceptor pairs, genetically coded donor-acceptor pairs have the advantage that they do not have to be taken up into living cells via an active transport mechanism or by permeabilization of the cell membrane. Thus, genetically coded donor-acceptor pairs can be used non-invasively.

In addition, genetically coded donor-acceptor pairs can be specifically localized in the desired cell compartments or fused to any target protein by fusion with suitable signal sequences.

Further, in accordance with the invention, a method is provided for detecting oxygen, pH, halide ions, temperature and/or flavin using a FRET donor-acceptor pair in accordance with one of claims 1 to 3, wherein at least one fluorescence protein is stable with respect to oxygen, pH, halide ions, temperature and/or flavin.

The term "detection" as used below should on the one hand be understood to mean that one of the factors oxygen, pH, halide ions, temperature and/or flavin is determined. On the other hand, the term "detection" also means measurement of one of the factors. This is accomplished, for example, by calculating a ratio of the two fluorescence maxima of the at least two fluorescence proteins, whereby the ratio changes in the event that the factor to be measured changes.

As already mentioned, the donor-acceptor pair of the invention or its use means that for the first time, a method is provided for measuring oxygen in biological systems by means of fluorescence proteins, emphatically improving detection of the factors pH, halide ions, temperature and/or flavin.

In one embodiment of the invention, detection is carried out by means of fluorescence resonance energy transfer after excitation with light at a wavelength in the range 370 nm to 450 nm.

This is particularly the case in the event that a FbFP protein acts as the donor, since these will be excited by light at a wavelength in the range 370 nm to 450 nm, in particular by light at a wavelength in the range 370 nm to 390 nm.

Further advantages and advantageous embodiments of the method of the invention will become apparent from the figures and exemplary examples and from the following description. It should be noted that the figures and exemplary examples are purely descriptive in nature and should not be considered to limit the invention to any specific form.

The donor absorbs light emitted by a light source and then re-emits it at a longer wavelength. The absorption maximum of the acceptor lies in this emission spectrum, so that it can absorb the radiated energy. In total, then, observing an emission from the acceptor means that an energy transfer from donor to acceptor known as FRET is being observed.

Figure 2:
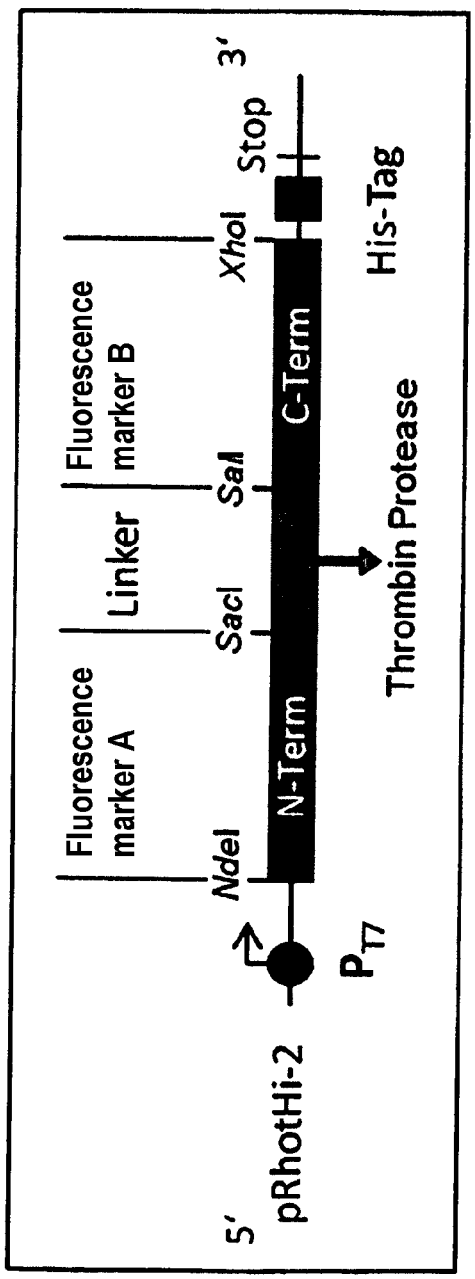
FIG. 2 shows a diagrammatic representation of the YFP-FbFP fusion protein.

FIG. 2 shows a diagrammatic representation of the YFP-FbFP fusion protein (SEQ ID No. 10). A translational fusion in which the FbFP fluorescence domain (SEQ ID No. 4) is fused C-terminally to the target protein YFP (SEQ ID No. 2) is generated in order to investigate whether the combination of the two proteins is a suitable novel FRET pair. To this end, the two proteins were bonded via a linker (SEQ ID No. 15 and 16) for this purpose.

Figure 3:
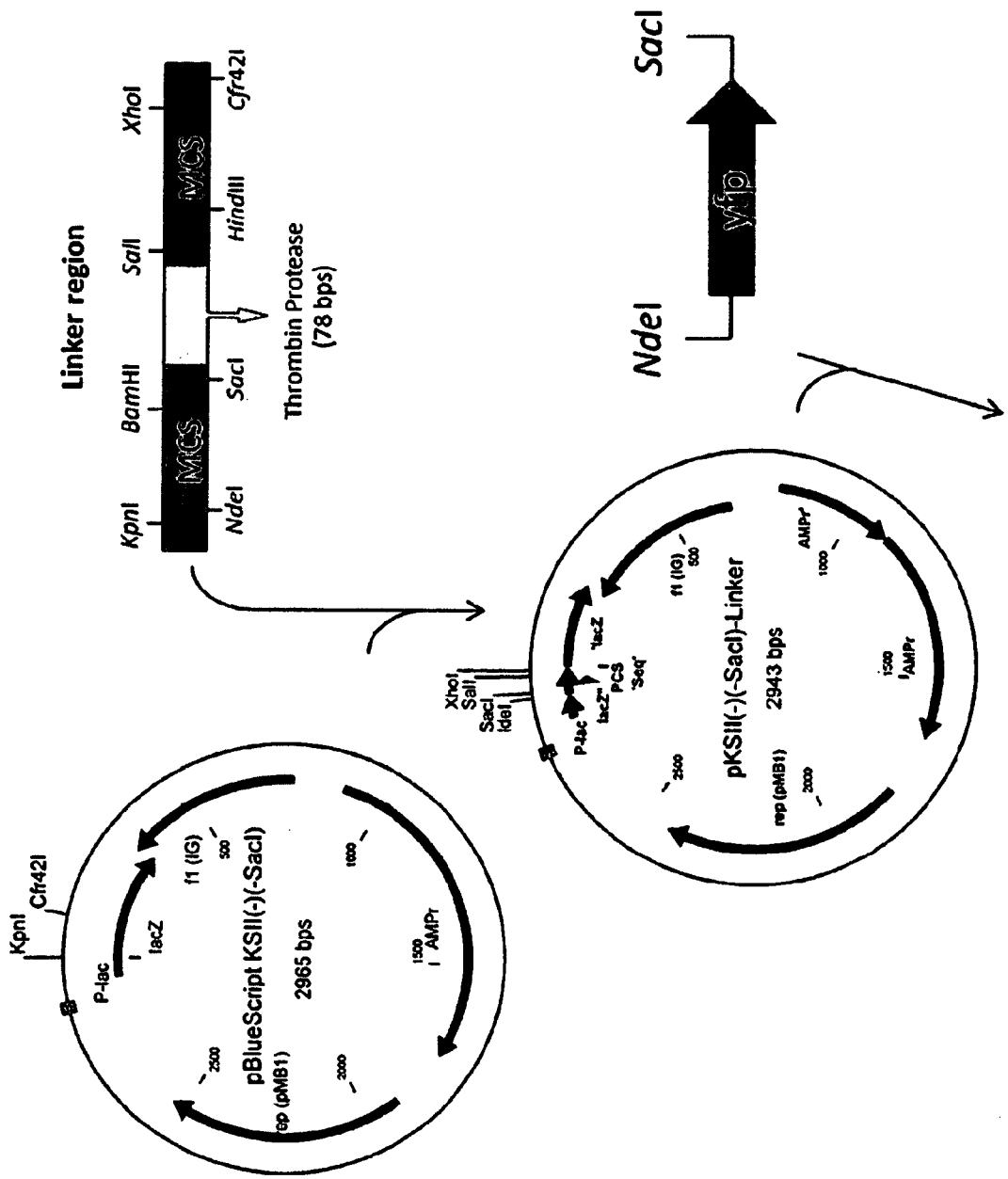
FIGS. 3 and 4 show a cloning strategy for the production of the YFP-FbFP fusion protein.
Figure 4:
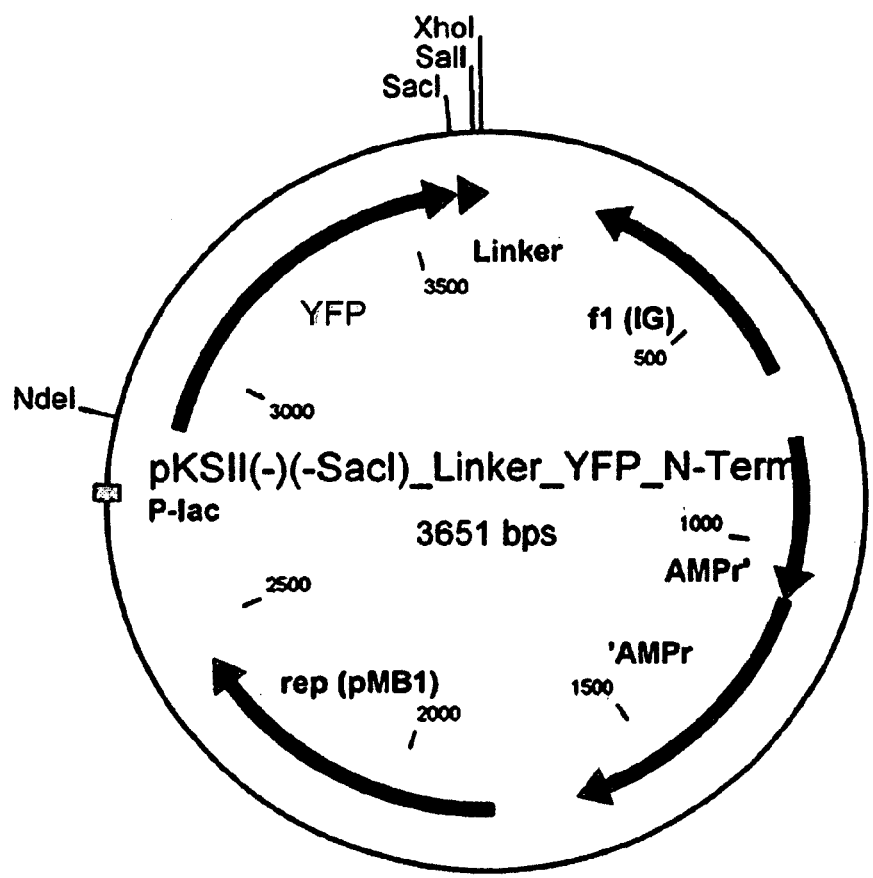

FIG. 3 and FIG. 4 show a cloning strategy for the production of the YFP-FbFP fusion protein (SEQ ID No. 10).

The fluorescence domains FbFP and YFP were amplified by means of PCR using modified primers (SEQ ID No. 11-14) and new restriction cleavage sites were generated. Cloning of the individual modules and the linker (SEQ ID No. 15 and 16) was carried out in the cloning vector pBlueScript KSII(−), which allows for blue-white selection in $E.\ coli$ DH5α cells.

Figure 5:
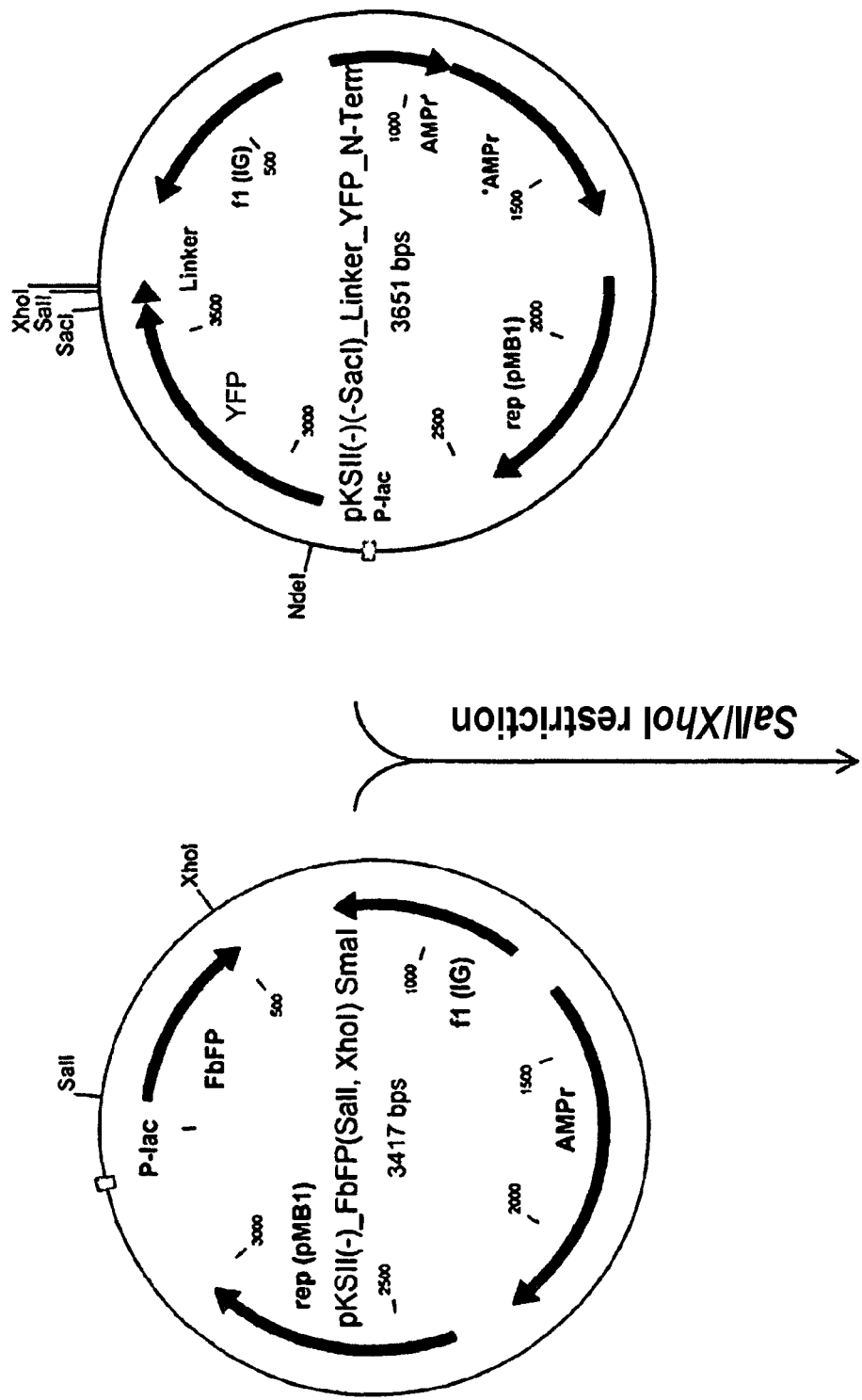
FIGS. 5 and 6 show a cloning strategy for the production of the YFP-FbFP fusion protein.
Figure 6:
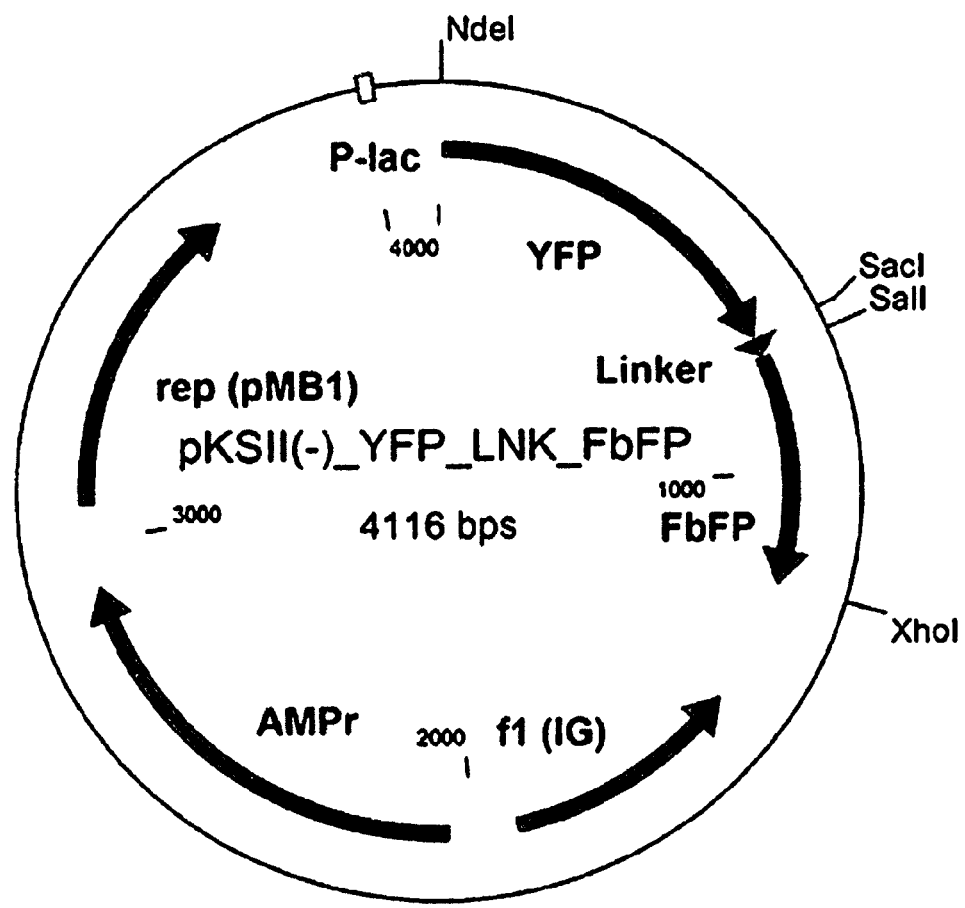

FIG. 5 and FIG. 6 show a cloning strategy for the production of the YFP-FbFP fusion (SEQ ID No. 9).

The map shows the final fusion of the FbFP (SEQ ID No. 3) with YFP (SEQ ID No. 1) by restriction digestion with the restriction endonucleases SalI/XhoI and subsequent ligation in pBlueScript KSII(−).

Figure 7:
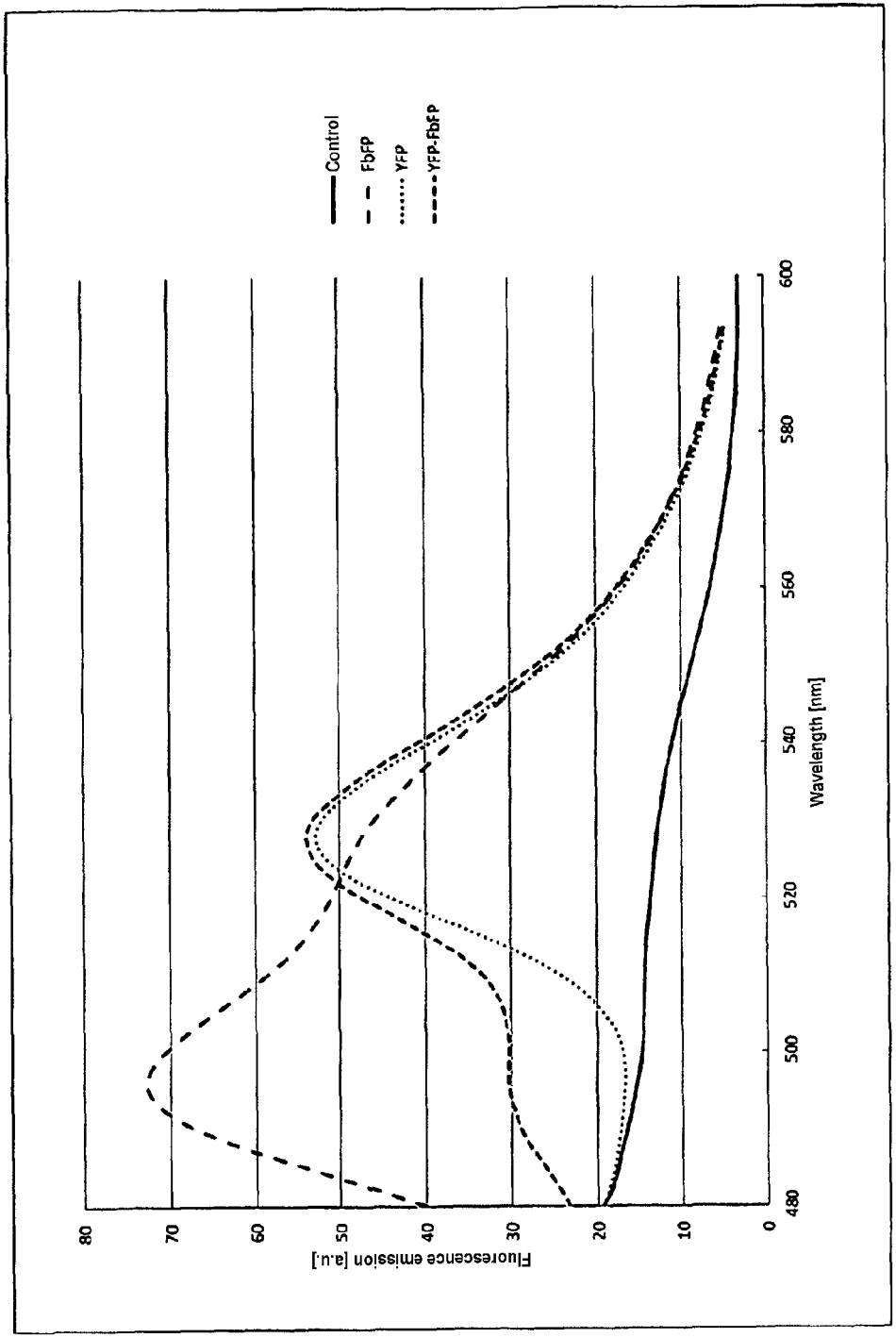
FIG. 7 shows the in vivo fluorescence of the YFP-FbFP fusion protein.

FIG. 7 shows the in vivo fluorescence of the YFP-FbFP fusion protein (SEQ ID No. 10).

It shows the in vivo fluorescence of the YFP-FbFP biosensor, the individual fluorescence proteins as well as the empty plasmid pRhotHi-2 following $T_7$ over-expression in $E.\ coli$ BL21(DE3) cells. The fluorescence of the cells was detected after excitation at λ=380 nm by means of a fluorescence photometer (Perkin Elmer). The profiles of the curves correspond to the specific fluorescence emissions of the proteins named in the Figure.

Figure 8:
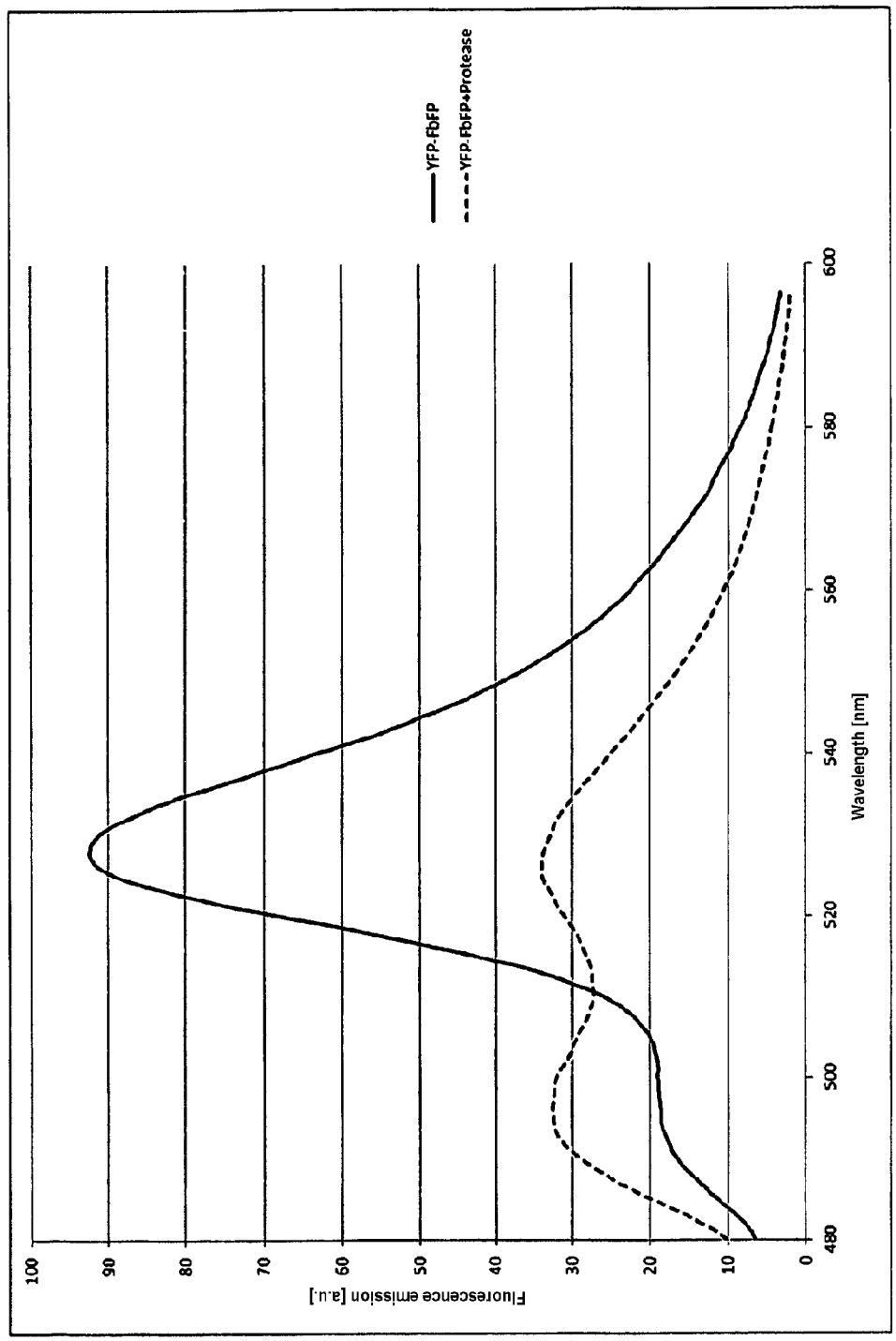
FIG. 8 shows the thrombin protease cleavage of the YFP-FbFP fusion protein.

FIG. 8 shows thrombin protease cleavage of the YFP-FbFP fusion protein (SEQ ID No. 10).

It shows the fluorescence measurement of the in vitro FRET fusion cleavage (YFP↓FbFP) by means of thrombin protease in the protein buffer. It also shows the fusion control without the addition of protease. Purified protein was used as the YFP-FbFP fusion, which was purified by affinity chromatography with the aid of the His$_6$ tag. The fluorescence emission was detected by means of a fluorescence photometer (Perkin Elmer) upon excitation at λ=380 nm; a YFP-FbFP absorption at 380 nm of 0.1 was used; the thrombin protease concentration was 1 u/μL.

FIG. 9 shows the fluorescence photometric measurement of Na$_2$S$_2$O$_4$ reduction of the YFP chromophore.

It shows the fluorescence emission for reduction of the YFP-FbFP biosensor (SEQ ID No. 10) with 50 mM Na$_2$S$_2$O$_4$ in protein buffer (10 mM NaH$_2$PO$_4$; 10 mM NaCl; pH 8). The fluorescence emission was detected by means of a fluorescence photometer (Perkin Elmer) upon excitation at λ=380 nm; a YFP-FbFP absorption at 380 nm of 0.1 was used. In addition, the fluorescence emission of the fusion was determined prior to adding the sodium dithionite (dashed line).

Figure 10:
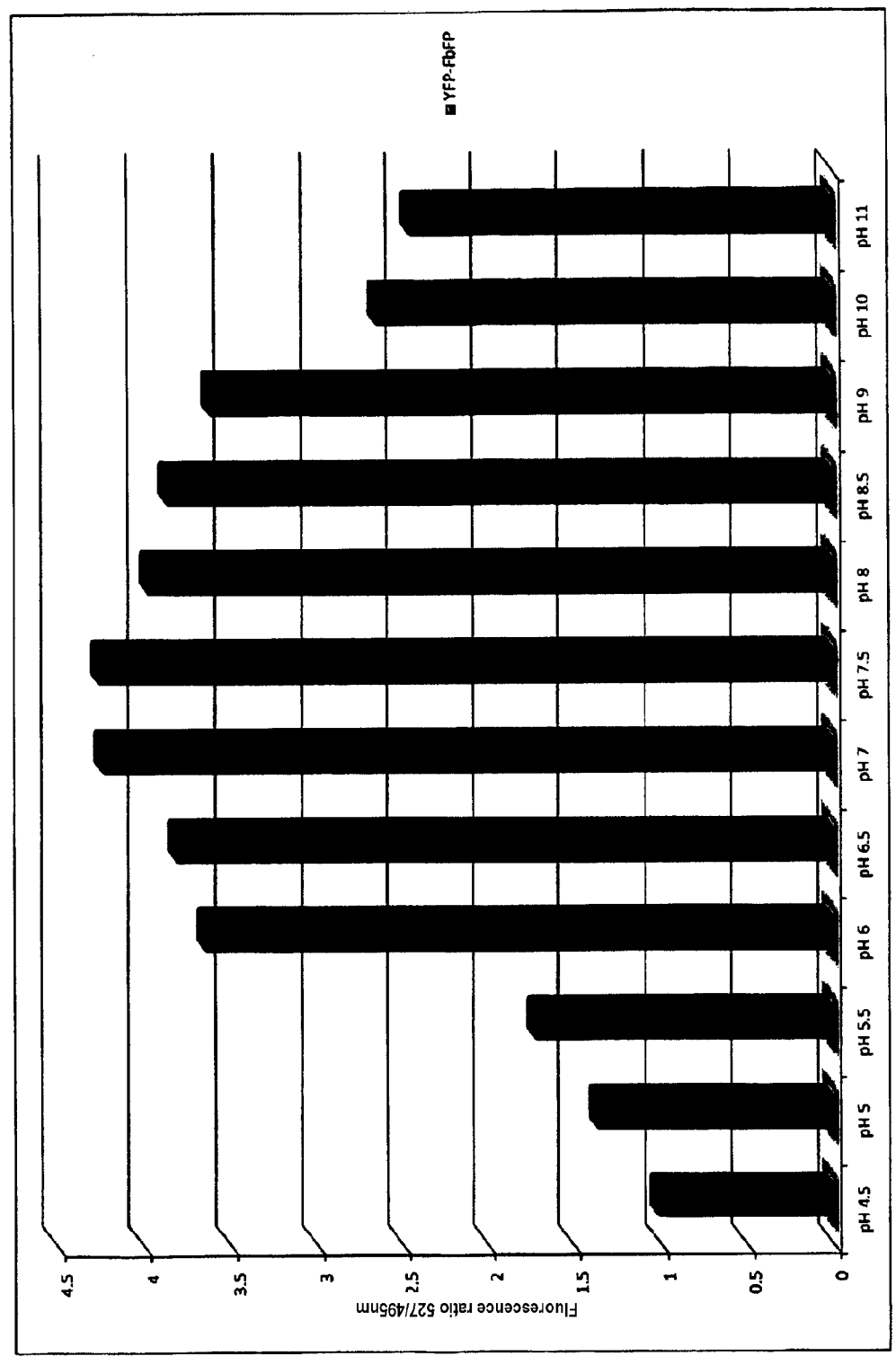
FIG. 10 shows the in vitro pH fluorescence measurement of the YFP-FbFP fusion protein.

FIG. 10 shows the in vitro pH fluorescence measurement of the YFP-FbFP fusion protein (SEQ ID No. 10).

This shows the calculated 527 nm/495 nm fluorescence ratio of the YFP (SEQ ID No. 2) and FbFP (SEQ ID No. 4) emission maxima of the in vitro measurement of the pH stability of the YFP-FbFP FRET fusion (SEQ ID No. 10) in a pH range of 4.5 to 11. The fluorescence emission of the fusion was detected by excitation of the purified protein at λ=380 nm with the aid of the Perkin Elmer fluorescence photometer. The 380 nm absorption of the protein was set at 0.1 in protein buffer and measured.

Figure 11:
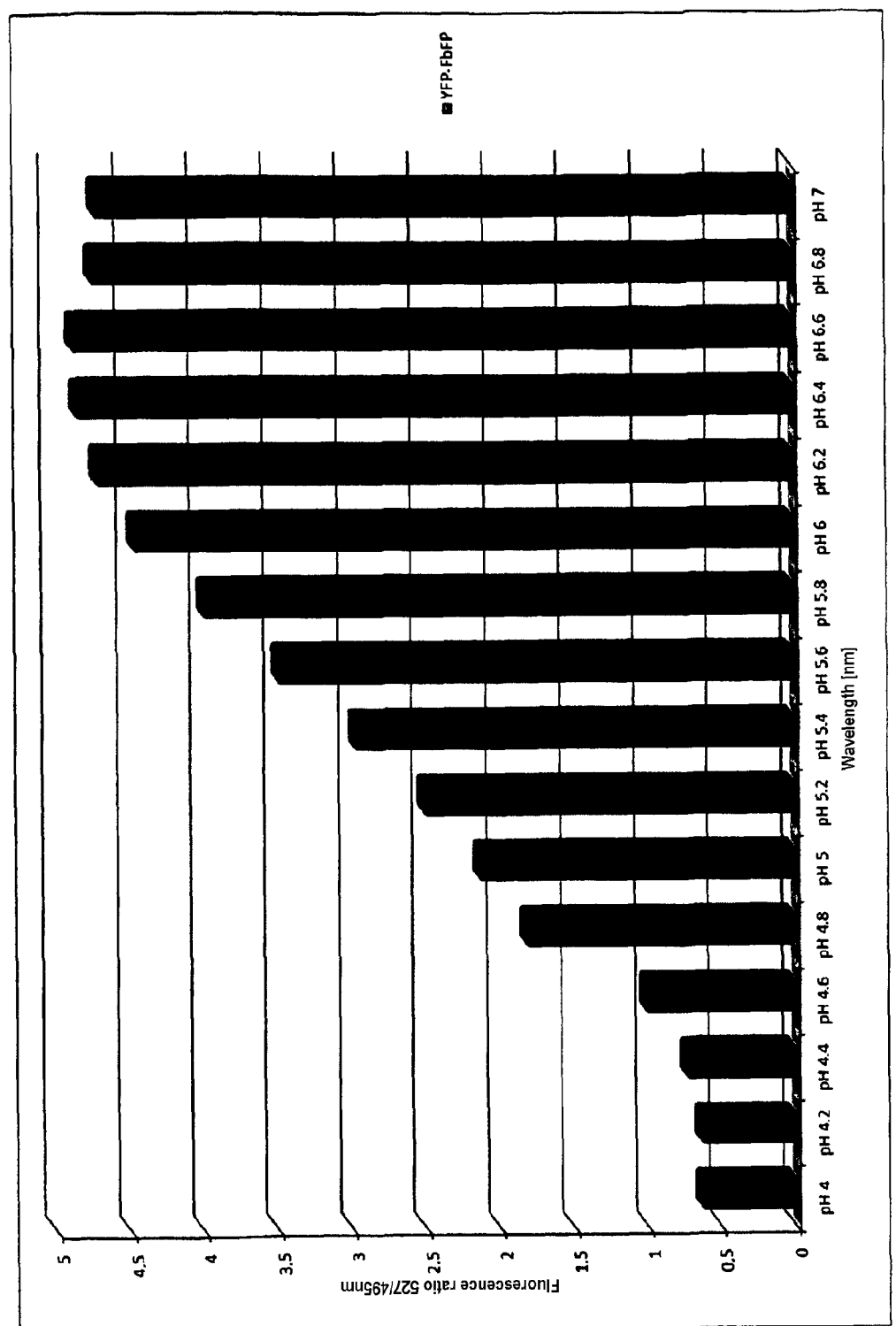
FIG. 11 shows the in vitro pH stability measurement of the YFP-FbFP fusion protein.

FIG. 11 shows the in vitro pH stability measurement of the YFP-FbFP fusion protein (SEQ ID No. 10).

This shows the calculated 527 nm/495 nm fluorescence ratio of the YFP (SEQ ID No. 2) and FbFP (SEQ ID No. 4) emission maxima of the in vitro measurement of the pH stability of the YFP-FbFP FRET fusion in a pH range of 4 to 7. The fluorescence emission of the fusion was detected by excitation of the purified protein at λ=380 nm with the aid of the Perkin Elmer fluorescence photometer. The absorption at 527 nm of the protein was set at 0.1 in protein buffer and measured.

Figure 12:
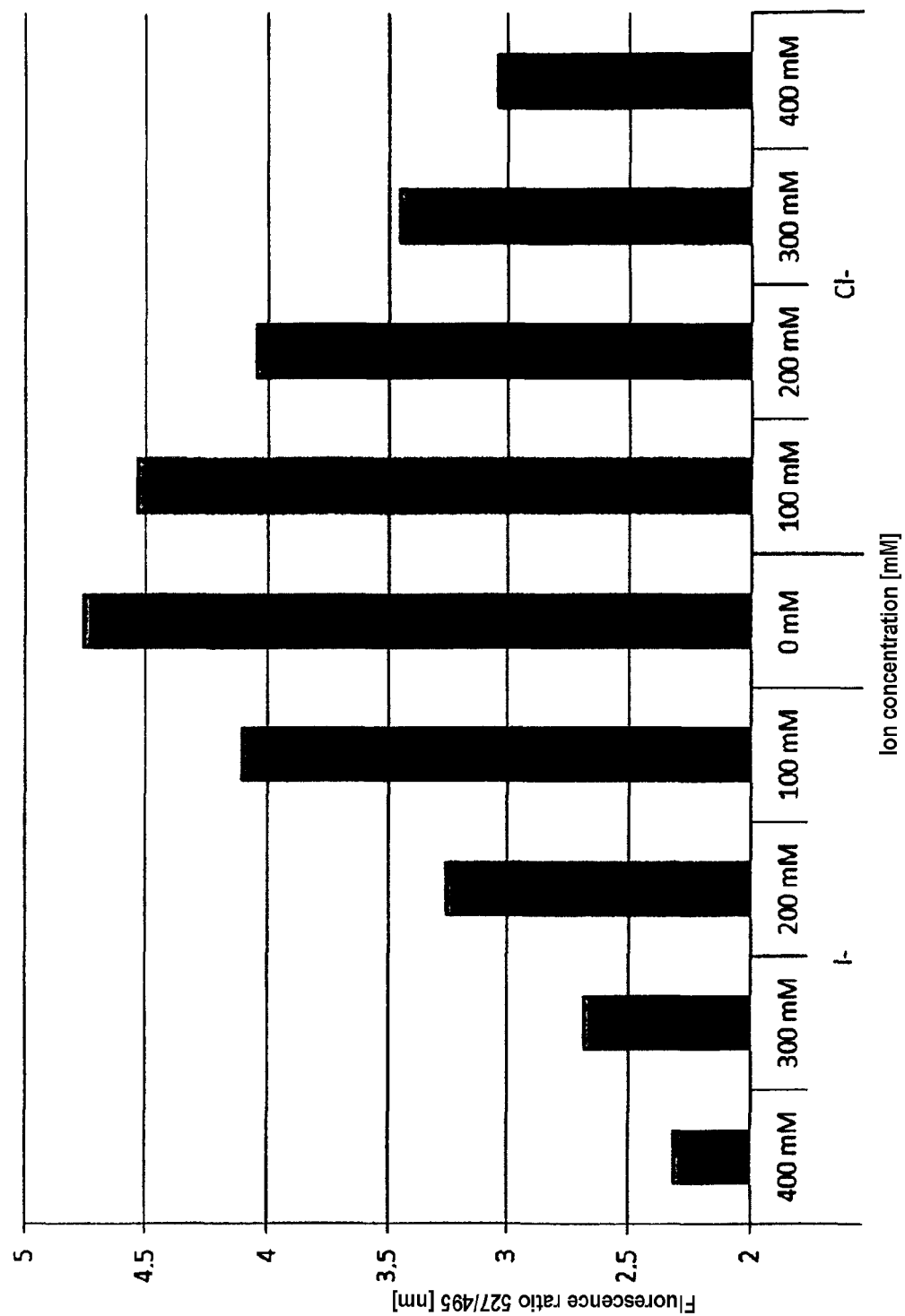
FIG. 12 shows a fluorescence photometric measurement for determining the suitability of the YFP-FbFP fusion protein as an ion biosensor.

FIG. 12 shows a fluorescence photometric measurement to investigate the suitability of the YFP-FbFP fusion protein (SEQ ID No. 10) as an ion biosensor.

It shows, as columns, the calculated 527 nm/495 nm fluorescence ratio of the emission maxima of YFP (SEQ ID No. 2) and FbFP (SEQ ID No. 4) for the in vitro measurement of the halide ion stability of the YFP-FbFP fusion protein (SEQ ID No. 10) at stepwise increasing iodide and chloride ion concentrations from 0 to 400 nM. The fluorescence emission of the fusion was detected upon excitation of the purified proteins at λ=380 nm with the aid of the Perkin Elmer fluorescence photometer. The 527 nm absorption of the protein was set at 0.1 in protein buffer and measured.

Figure 13:
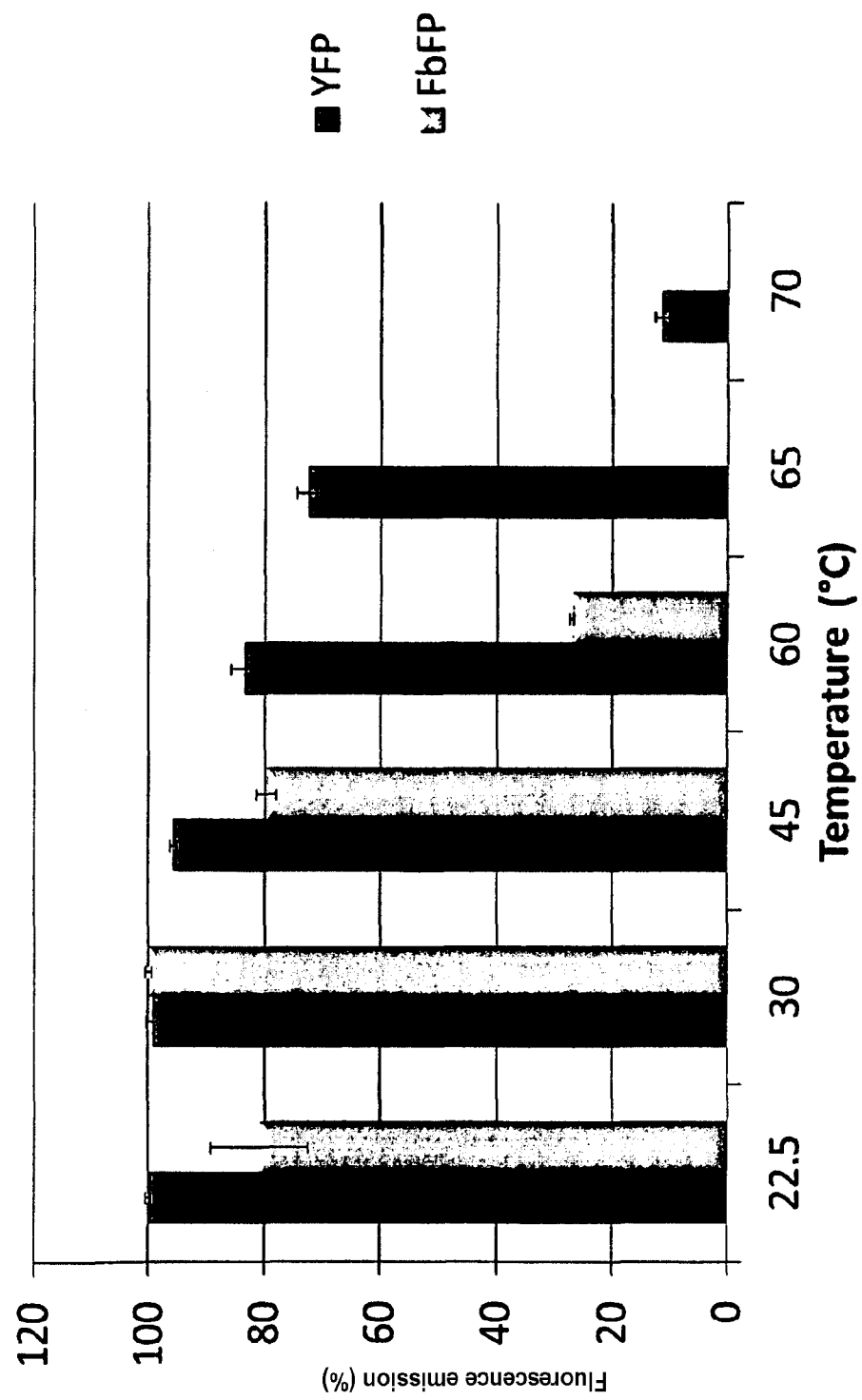
FIG. 13 shows a temperature stability test for YFP and FbFP.

FIG. 13 shows the temperature stability test for YFP and FbFP.

It shows the fluorescence emission as a percentage of the YFPs (SEQ ID No. 2) and the FbFPs (SEQ ID No. 4) as a function of temperature in order to investigate the suitability of the YFP-FbFP fusion protein as a temperature biosensor.

Exemplary Embodiments i. Construction of Biosensors

In order to be able to investigate whether the FMN-based fluorescence reporter protein FbFP (SEQ ID No. 4) was suitable for use as a novel biosensor, a translational fusion (SEQ ID No. 9) was generated in which the FbFP fluorescence domain (SEQ ID No. 4) was fused C-terminally to the target protein YFP (SEQ ID No. 2). To this end, the two proteins were linked by means of a linker (SEQ ID No. 15 and 16) which contained a "multiple cloning site" (MCS) with cleavage sites for the restriction endonucleases KpnI, NdeI, BamHI, SacI, SalI, HindIII, XhoI and Cfr42I. In order to express the YFP-FbFP fusion protein, the expression vector pRhotHi-2 was also selected. The fusion protein was also provided with a His$_6$ tag, so that the recombinant protein could easily be purified by affinity chromatographic methods. All of the cloning steps were carried out in the cloning vector pBluescript KSII(−).

2. Characterization of the YFP-FbFP Fusion Protein (SEQ ID No. 10)

In order to be able to show that a functional FRET system could be produced with the YFP-FbFP fusion protein, initially an in vivo characterization of the fusion protein was carried out in the gram-negative bacterium *E. coli*. To this end, the plasmid pRhotHi-2_YFP_FbFP was over-expressed in the *E. coli* strain BL21DE3 by adding IPTG.

The fluorescence emission was detected and recorded in the fluorescence photometer after excitation with blue light (λ=380 nm). For the control, the fluorescence proteins FbFP (SEQ ID No. 4) and YFP (SEQ ID No. 2) were expressed individually and their fluorescence spectra were also recorded at this excitation. The negative control was the fluorescence of the empty plasmid pRhotHi-2, as can be seen in FIG. 7.

Comparing the emission maxima of FbFP and YFP in the YFP-FbFP fusion protein with the maxima of the respective non-fused fluorescence proteins, surprisingly, a significant difference was seen which is due to the radiationless transfer of energy from FbFP to YFP. In this regard, after specific excitation of the FbFP chromophore, it shows a low fluorescence emission of FbFP (emission maximum 495 nm) and a significant fluorescence emission of YFP (emission maximum at 527 nm).

3. Closer Investigation of Fluorescence Properties of YFP-FbFP Fusion Protein

In order to examine the fluorescence properties of the YFP-FbFP fusion protein (SEQ ID No. 10) in more detail, the fusion was purified by affinity chromatography with the aid of a His$_6$ tag and taken up in protein buffer (10 mM NaH$_2$PO$_4$, 10 Mm NaCl, pH 8) in order to be able to carry out the necessary investigations. In order to demonstrate that the fluorescence of the FRET acceptor YFP (SEQ ID No. 2) is due to energy transfer from the FRET donor FbFP (SEQ ID No. 4) after specific excitation of the donor chromophore, the two fluorescence domains of the YFP-FbFP fusion protein were once again separated using thrombin protease. Since there is a thrombin protease cleavage site in the linker region of the YFP-FbFP fusion protein, the spatial separation of the fluorescence domains due to the thrombin protease resulted in a reduced fluorescence emission from YFP (λ=527 nm) and an increased fluorescence emission from FbFP (λ=495 nm). This should be the case, since in the event of proteolytic separation, the maximum Förster radius of 100 Å is exceeded and thus the energy of the FRET donor FbFP after specific excitation (λ=380 nm) can no longer be transferred directly to the FRET acceptor YFP, but the FbFP emits the light at λ=495 nm in the form of fluorescence. As was shown in the corresponding experiment (FIG. 8), the proteolytic separation of the FbFP from the YFP domains gave the expected result. The complete protease digestion of the YFP-FbFP fusion protein was then confirmed by SDS-PAGE, which separated the proteins in order of size. It could clearly be seen that after proteolytic digestion, the YFP-FbFP fusion protein is no longer present as the fusion protein (~45 kDa) but can only be detected as two separate fluorescence proteins FbFP (~17 kDa) and YFP (~27 kDa). The respective non-fused fluorescence proteins were applied as a reference in order to verify the effect of protease cleavage.

4. Use of YFP-FbFP Fusion Protein as $O_2$ Biosensor

In order to check whether the YFP-FbFP fusion protein produced (SEQ ID No. 10) could be used as a novel $O_2$ biosensor, the YFP chromophore was reduced by adding sodium dithionite, whereupon the fluorescence from this domain was completely inhibited. At the same time, the reduction medium completely bound the dissolved oxygen, so that re-oxidation of the chromophore was severely inhibited. FIG. 9 shows the fluorescence spectrum of the YFP-FbFP fusion protein (SEQ ID No. 10) before and after reduction with sodium dithionite at a specific excitation of the FbFP chromophore. The fluorescence spectrum shows that prior to reduction of the YFP chromophore, the specific YFP fluorescence emission at $\lambda=527$ nm can clearly be detected in the YFP-FbFP fusion protein. Further, it can be seen that the FbFP fluorescence emission in the YFP-FbFP fusion protein at $\lambda=495$ nm is increased after adding sodium dithionite, which can be attributed to reduced energy transfer from the donor to the YFP receptor. This experiment demonstrates a stark reduction in the YFP fluorescence signal as a function of oxygen. Because of these results, it could be shown that surprisingly and for the first time with the novel YFP-FbFP fusion protein, it is possible to assay oxygen by the relative ratio of the signals from both fluorescence domains.

5. Use of YFP-FbFP Fusion Protein as pH Biosensor

In order to be able to characterize the dependency of the fluorescence of the biosensor on the pH, the genes YFP (SEQ ID No. 1), FbFP (SEQ ID No. 3) and YFP-FbFP (SEQ ID No. 9) were over-expressed in pRhotHi-2 in *E. coli* BL21(DE)3 cells, induced by IPTG, lysed and purified by affinity chromatography using an $His_6$ tag. The fluorescence intensity change with pH was characterized in more detail with the aid of a pH universal buffer. To this end, the various fluorescence intensities of the YFP-FbFP fusion protein and the respective individual fluorescence reporter proteins were detected under the UV lamp and in the fluorescence photometer at pHs of 4.5, 5, 5.5, 6, 6.5, 7, 7.5, 8, 8.5, 9, 10, 11 and 12. FIGS. 10 and 11 show that the novel biosensor is highly suitable for extremely sensitive pH determination. The diagram shown in FIG. 10 shows the ratio of the fluorescence maxima of YFP and FbFP in the YFP-FbFP fusion protein (SEQ ID No. 10). It can clearly be seen that the measurement range of the novel biosensor extends from 4.0 to 7.0, which covers the whole physiological range of living organisms. The YFP-FbFP fluorescence ratio drops by a factor of 2.5 from a pH of 7 to a pH of 4. This effect can be explained by a destabilizing effect on the YFP chromophore of the pH-dependent protonation of the chromophore. Additional fluorescence measurements with the individual fluorescence proteins YFP and FbFP also provide evidence of this destabilizing effect of the pH on the YFP fluorescence signal, while the fluorescence emission for FbFP over a pH range of 8 to 4.5 hardly changes. These data thus clearly prove that the YFP-FbFP fusion protein (SEQ ID No. 10) can be used for a sensitive assay of pH both in vitro and in vivo.

6. Use of YFP-FbFP Fusion Protein as a Halide Ion Biosensor

The question of whether the fluorescence emission of FbFP (SEQ ID No. 4) could also be influenced by the ion concentration was investigated using purified FbFP. To this end, the expression vector pRhotHi-2_fbfp+$His_6$ was transformed in the expression strain *E. coli* BL21(DE), the gene was over-expressed, purified, concentrated and buffered. Successful expression and purification was checked by SDS-PAGE (results not shown). In order to determine the fluorescence emission of FbFP as a function of ion concentration, a quantity of protein corresponding to an absorption ($\lambda=450$ nm) of 0.1 was dissolved in one mL of pH universal buffer. The pH of the protein buffer had been adjusted to 8.0. The test ion concentrations were obtained by dissolving appropriate quantities of sodium chloride or sodium iodide in this buffer. The measurement was then carried out in a fluorescence photometer (LS 50 B, Perkin Elmer) at an excitation wavelength of 380 nm. This showed that the fluorescence emission of FbFP was barely influenced by the test ion concentrations, since the relative fluorescence emission as a function of ion concentration was almost constant over an approximately 150 unit range (data not shown).

Because of the constant nature of the fluorescence emission of FbFP over the tested ion concentration range and the simultaneous sensitivity of the FRET partner YFP (SEQ ID No. 2) to exactly these conditions, this means that a basic requirement for the use of this system as a biosensor has been fulfilled, since the ion concentration dictates the specific ratio of the two emission maxima of FbFP and YFP. In order to check this in vitro, the fluorescence emission of the YFP-FbFP fusion protein (SEQ ID No. 10) was measured by fluorescence photometry as a function of various ion concentrations. The characterization of the YFP-FbFP fusion protein was carried out at an excitation wavelength of 380 nm. This ratio, produced from the emission maxima at 495 (FbFP) and 527 nm (YFP), shows that the YFP-FbFP fusion protein is also surprisingly sensitive and reacts to different halide ion concentrations. The bar chart (FIG. 12) shows that the ratios of the emission maxima of FbFP and YFP drop with increasing concentration of both chloride ions and iodide ions. The fusion reacts to the same concentration of iodide ions in a more sensitive manner than chloride ions, which is shown by the much stronger decay in the best fit lines over the respective series of measurements. For the measurement of the different iodide ion concentrations, this is 0.6302 and in the case of chloride ion concentrations, it is only 0.4512. The reduction in the fluorescence ratio of the two fluorescence domains is thus due to the sensitivity of the YFP to ions as this shows that the emission of FbFP is almost constant over the tested concentration range. The results shown here illustrate that the YFP-FbFP fusion protein reacts in a sensitive manner to different iodide and chloride ion concentrations, whereby a higher ion concentration results in a reduction in the ratio ($\lambda$ 527/495) of the emission maxima.

7. Use of YFP-FbFP Fusion Protein as Temperature Biosensor

To this end, the two fluorescence proteins FbFP (SEQ ID No. 4) and YFP (SEQ ID No. 2) were over-expressed in *E. coli* BL21(DE3) cells, lysed and purified by affinity chromatography with the help of an $His_6$ tag. After transfer by re-buffering into the protein buffer (10 mM $NaH_2PO_4$, 10 Mm NaCl, pH 8), the proteins, brought to an absorption of 0.1, were incubated at the respective temperatures for 5 minutes and then the fluorescence emission was determined photometrically with the aid of the Perkin Elmer photometer. As can be seen in FIG. 13, the YFP protein is much more stable at high temperatures than the FbFP protein, since YFP still exhibits 82% to 75% fluorescence emission at 60° C. to 65° C. compared with the maximum emission at 22.5° C. With FbFP, the fluorescence emission reduces significantly to 27%. At 65° C., this fluorescence protein exhibits no further fluorescence.

LITERATURE

BAIRD, G. S., ZACHARIAS, D. A. and TSIEN, R. Y. (1999). Circular permutation and receptor insertion within green fluorescent proteins. *Proc Natl Acad Sci USA* 96, 11241-11246.

MANK, M., REIFF, D. F., HEIM, N., FRIEDRICH, M. W., BORST, A. and GRIESBECK, O. (2006). A FRET-based calcium biosensor with fast signal kinetics and high fluorescence change. *Biophys J* 90, 1790-1796.

PICKUP, J. C., HUSSAIN, F., EVANS, N. D., ROLINSKI, O. J. and BIRCH, D. J. (2005). Fluorescence-based glucose sensors. *Biosens Bioelectron* 20, 2555-2565.

YANG, T., OKU, M., AKEYAMA, N., ITOYAMA, A., YURIMOTO, H., KUGE, S., FUJIKI, Y. and SAKAI, Y. (2010). A Novel Fluorescent Sensor Protein for Visualization of Redox States in the Cytoplasm and in Peroxisomes. *Mol Cell Biol*

The invention claimed is:

1. A FRET donor-acceptor pair for use as a biosensor, comprising at least two fluorescence proteins, wherein at least one fluorescence protein is stable with respect to a parameter to be detected by the biosensor and at least one fluorescence protein is unstable with respect to the parameter to be detected by the biosensor, wherein at least one fluorescence protein of the FRET donor-acceptor pair is oxygen-independent and at least one fluorescence protein of the FRET donor-acceptor pair is oxygen-dependent.

2. The FRET donor-acceptor pair as claimed in claim 1, wherein at least two fluorescence proteins of the FRET donor-acceptor pair carry different chromophores.

* * * * *